United States Patent
Pichardo et al.

(10) Patent No.: US 12,190,858 B2
(45) Date of Patent: Jan. 7, 2025

(54) SYSTEMS AND METHODS FOR CONTROLLING DIRECTIONAL PROPERTIES OF ULTRASOUND TRANSDUCERS VIA BIPHASIC ACTUATION

(71) Applicant: NOVUSTX DEVICES INC., Calgary (CA)

(72) Inventors: Samuel Pichardo, Calgary (CA); Laura Curiel, Calgary (CA); Sagid Alberto Delgado Amparano, Calgary (CA)

(73) Assignee: NOVUSTX DEVICES INC., Calgary (CA)

( * ) Notice: Subject to any disclaimer, the term of this patent is extended or adjusted under 35 U.S.C. 154(b) by 273 days.

(21) Appl. No.: 17/791,406

(22) PCT Filed: Jan. 8, 2021

(86) PCT No.: PCT/CA2021/050014
§ 371 (c)(1),
(2) Date: Jul. 7, 2022

(87) PCT Pub. No.: WO2021/138745
PCT Pub. Date: Jul. 15, 2021

(65) Prior Publication Data
US 2023/0033799 A1    Feb. 2, 2023

Related U.S. Application Data

(60) Provisional application No. 62/959,616, filed on Jan. 10, 2020.

(51) Int. Cl.
*G10K 11/34*    (2006.01)
*A61B 8/00*    (2006.01)
(Continued)

(52) U.S. Cl.
CPC .......... *G10K 11/346* (2013.01); *A61B 8/4483* (2013.01); *A61B 8/4488* (2013.01);
(Continued)

(58) Field of Classification Search
CPC .... G01N 29/221; G01N 29/225; G01N 29/26; G01N 29/346; G01N 29/348;
(Continued)

(56) References Cited

U.S. PATENT DOCUMENTS

| | | |
|---|---|---|
| 5,322,068 A | 6/1994 | Thiele et al. |
| 7,004,824 B1 | 2/2006 | Madanshetty |

(Continued)

FOREIGN PATENT DOCUMENTS

| | | | |
|---|---|---|---|
| WO | 2012156838 A1 | 11/2012 | |
| WO | WO-2015074153 A1 * | 5/2015 | ............... A61N 7/00 |

OTHER PUBLICATIONS

Hughes A, Hynynen K., "Design of patient-specific focused ultrasound arrays for non-invasive brain therapy with increased transskull transmission and steering range", Phys Med Biol. Aug. 3, 2017;62(17):L9-L19. doi: 10.1088/1361-6560/aa7cd5.

(Continued)

*Primary Examiner* — Benjamin R Schmitt
(74) *Attorney, Agent, or Firm* — HILL & SCHUMACHER

(57) ABSTRACT

Systems and methods are provided whereby a directional property of an ultrasound transducer element, such as a steering direction, is controlled according to a first driving waveform that is delivered to opposing propagation electrodes and a second driving waveform that is delivered to opposing lateral electrodes. The directional property may be controlled according a phase difference and/or relative amplitude between the first and second driving waveforms, and/or the selective actuation of one or more lateral elec- (Continued)

trodes when the lateral electrodes are defined in an array. The ultrasound transducer element may be a ring-shaped transducer element and a directional property associated with a focal region may be controlled. In some example embodiments, array elements of an ultrasound transducer array may each include propagation and lateral electrodes, with each array element being driven by respective first and second driving waveforms to focus the ultrasound energy emitted by the ultrasound transducer array.

30 Claims, 25 Drawing Sheets

(51) Int. Cl.
  *B06B 1/02* (2006.01)
  *B06B 1/06* (2006.01)
  *G01N 29/22* (2006.01)
  *G01N 29/26* (2006.01)
  *G01N 29/34* (2006.01)
  *G01S 7/52* (2006.01)
  *G10K 9/125* (2006.01)
(52) U.S. Cl.
  CPC .......... *A61B 8/4494* (2013.01); *B06B 1/0207* (2013.01); *B06B 1/0607* (2013.01); *B06B 1/0662* (2013.01); *B06B 1/0674* (2013.01); *G01N 29/221* (2013.01); *G01N 29/225* (2013.01); *G01N 29/26* (2013.01); *G01N 29/346* (2013.01); *G01N 29/348* (2013.01); *G01S 7/5202* (2013.01); *G10K 9/125* (2013.01); *G10K 11/343* (2013.01); *G10K 11/348* (2013.01); *B06B 2201/76* (2013.01)
(58) Field of Classification Search
  CPC ...... G10K 9/125; G10K 11/34; G10K 11/341; G10K 11/343; G10K 11/346; G10K 11/348; B06B 1/0207; B06B 1/0607; B06B 1/0662; A61B 8/4488; A61B 8/4483; A61B 8/4494
  See application file for complete search history.

(56) References Cited

U.S. PATENT DOCUMENTS

| | | | |
|---|---|---|---|
| 8,715,187 B2 | 5/2014 | Landberg Davis et al. | |
| 8,932,237 B2 | 1/2015 | Vitek et al. | |
| 9,177,543 B2 | 11/2015 | Vitek et al. | |
| 9,555,268 B2 | 1/2017 | Clark | |
| 9,852,727 B2 | 12/2017 | Vitek et al. | |
| 2007/0055160 A1 | 3/2007 | Ng | |
| 2019/0328360 A1* | 10/2019 | Ferin | B06B 1/0622 |

OTHER PUBLICATIONS

Maimbourg G, Houdouin A, Deffieux T, Tanter M, Aubry JF., "Steering Capabilities of an Acoustic Lens for Transcranial Therapy: Numerical and Experimental Studies", IEEE Trans Biomed Eng. Mar. 26, 2019. doi: 10.1109/TBME.2019.2907556. [Epub ahead of print].
Kim S, Kim H, Shim C, Lee HJ., "Improved Target Specificity of Transcranial Focused Ultrasound Stimulation (TSUS) using Double-Crossed Ultrasound Transducers", Conf Proc IEEE Eng Med Biol Soc. Jul. 2018;2018:2679-2682. doi: 10.1109/EMBC.2018.8512812.
Pichardo S, Silva RRC, Rubel O, Curiel L, "Efficient Driving of Piezoelectric Transducers Using a Biaxial Driving Techinque", (2015), Efficient Driving of Piezoelectric Transducers Using a Biaxial Driving Technique. PLoS One 10(9):e0139178, https://doi.org/10.1371/journal.pone.0139178.
Author Zhuochen Wang, "Dual-frequency Ultrasound Transducers for Medical Imaging", Publication date Oct. 18, 2016 https://repository.lib.ncsu.edu/bitstream/handle/1840.20/33245/etd.pdf?sequence=1.
Kamimura et al., "Feedback control of microbubble cavitation for ultrasound-mediated blood-brain barrier disruption in non-human primates under magnetic resonance guidance", J Cereb Blood Flow Metlab. Jul. 2019; 39(7): 1191-1203; Published online Jan. 30, 2018. doi: 10.1177/0271678X17753514, https://www.ncbi.nlm.nih.gov/pmc/articles/PMC6668523/.
Corrected Search Report for PCT/CA2021/050014 dated Jun. 28, 2021, 3 pages.

* cited by examiner

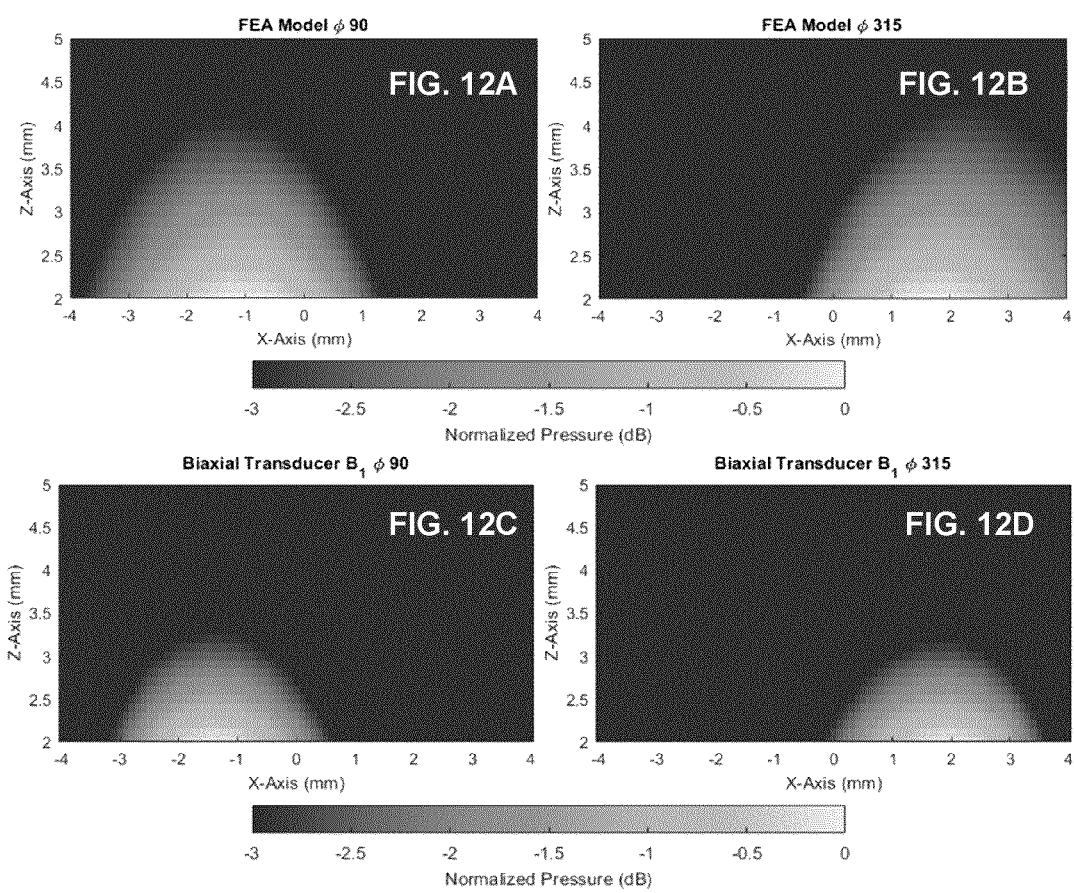

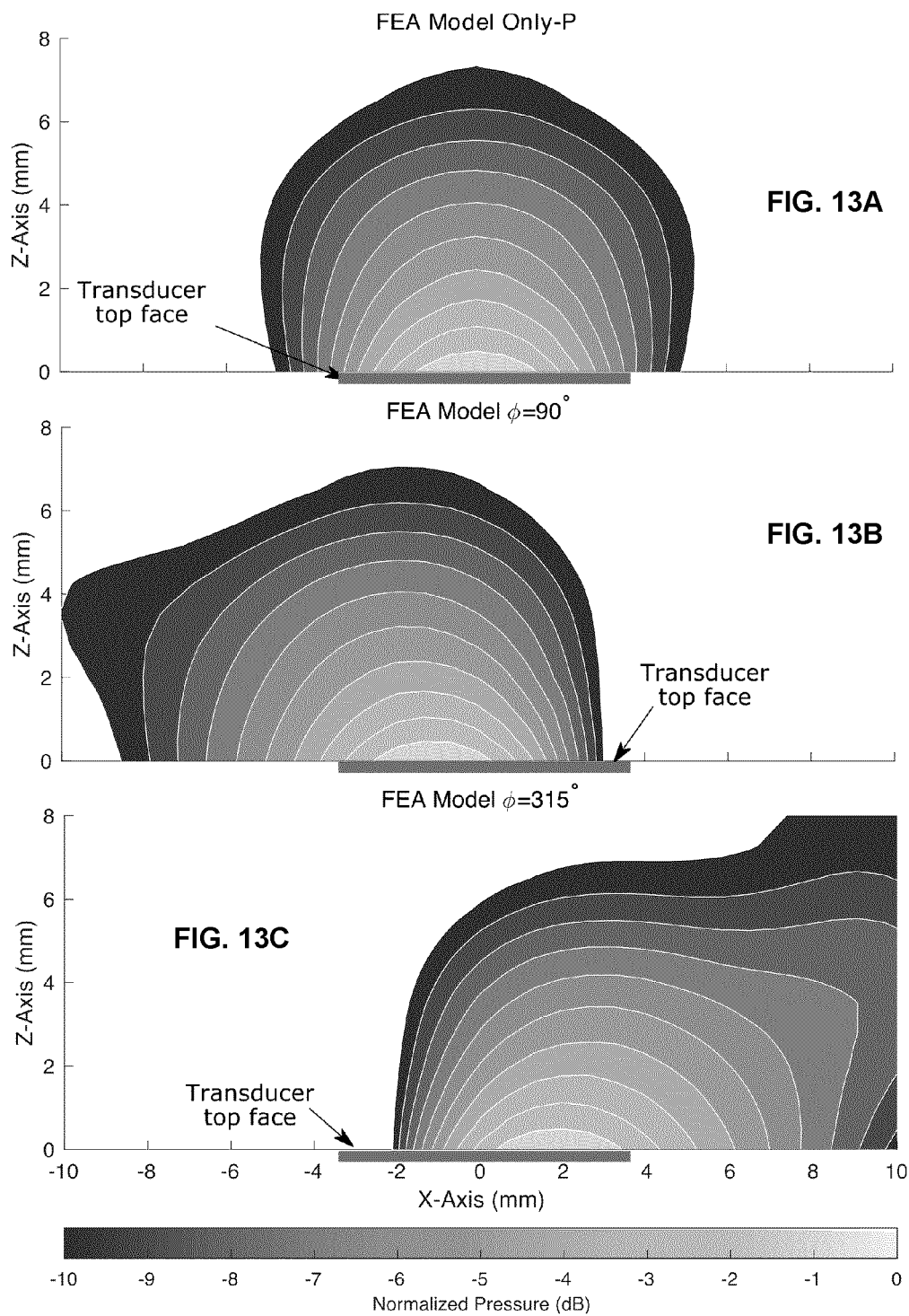

| $p_l$ (W) | Negative steering (left) | | | | Positive steering (right) | | | |
|---|---|---|---|---|---|---|---|---|
| | FEA model | | Experiments | | FEA model | | Experiments | |
| | $\phi$ (°) | $\gamma$ (°) | $\phi$ (°) | $\gamma$ (°) | $\phi$ (°) | $\gamma$ (°) | $\phi$ (°) | $\gamma$ (°) |
| 0.1 | 135 | -13.7 | 135 | -14.4(±1.2) | 315 | 18.3 | 315 | 14.4(±0.7) |
| 0.5 | 90 | -20.4 | 135 | -28.6(±1.8) | 315 | 31.9 | 270 | 26.8(±2.1) |
| 1.0 | 90 | -25.3 | 180 | -36.3(±4.0) | 315 | 40.8 | 270 | 32.4(±2.3) |

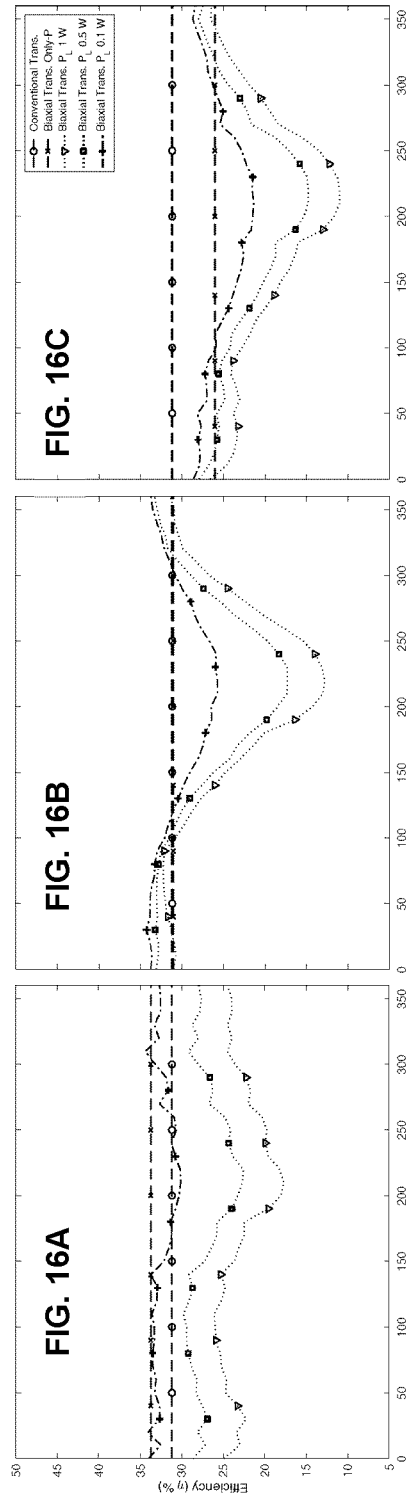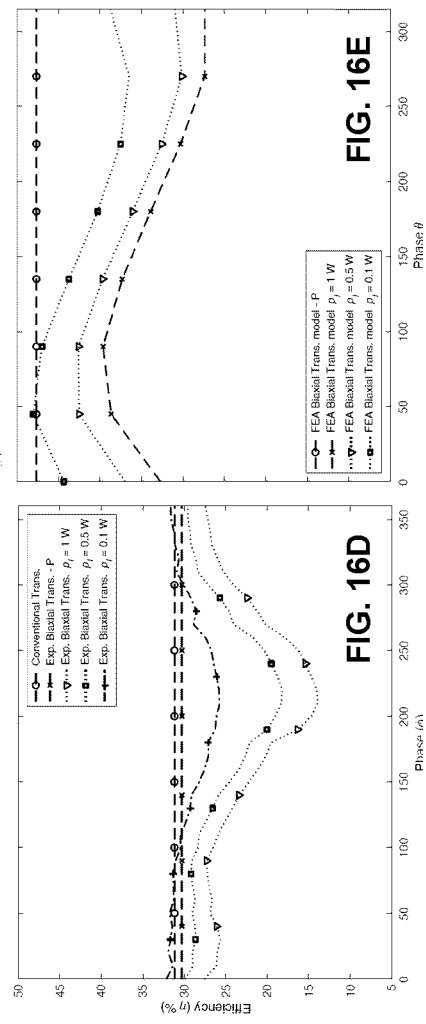
FIG. 16A
FIG. 16B
FIG. 16C
FIG. 16D
FIG. 16E

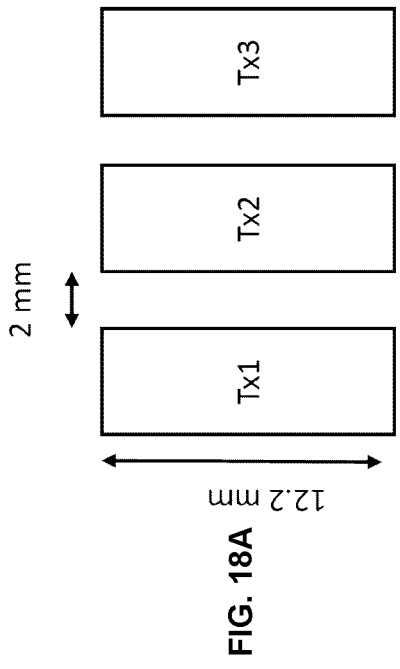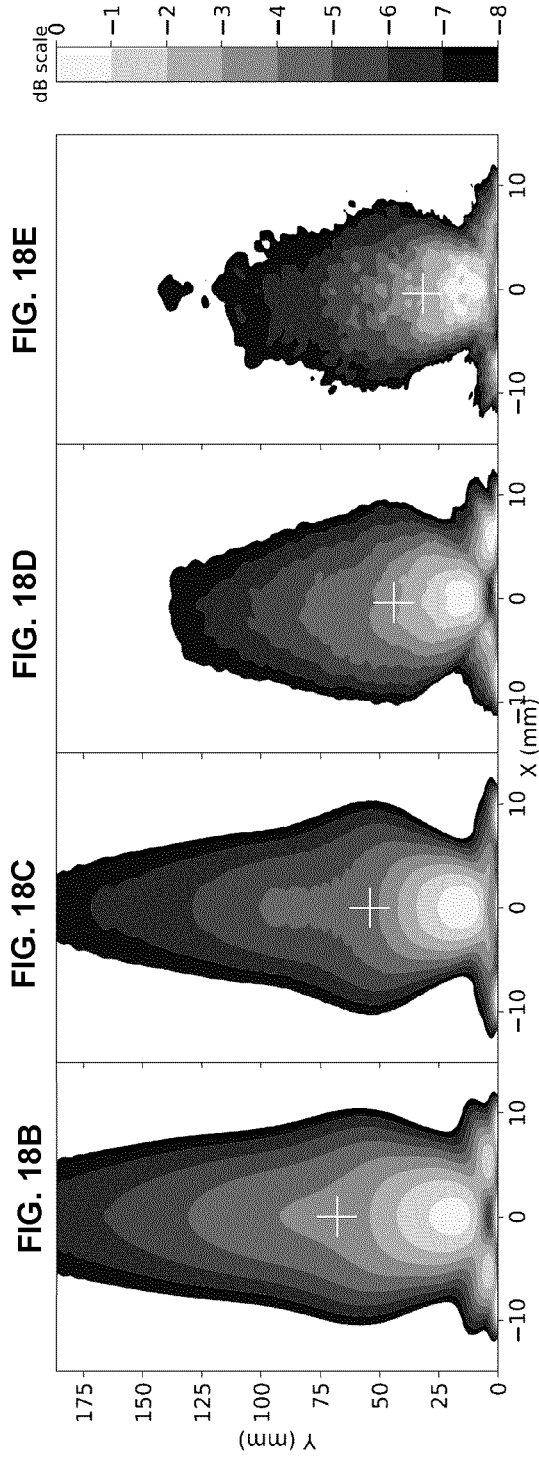

SYSTEMS AND METHODS FOR CONTROLLING DIRECTIONAL PROPERTIES OF ULTRASOUND TRANSDUCERS VIA BIPHASIC ACTUATION

CROSS-REFERENCE TO RELATED APPLICATION

This application is a National Phase application claiming the benefit of the international PCT Patent Application No. PCT/CA2021/050014, filed on January 8, 2021, in English, which claims priority to U.S. Provisional Application No. 62/959,616, titled "SYSTEMS AND METHODS FOR CONTROLLING DIRECTIONAL PROPERTIES OF ULTRASOUND TRANSDUCERS VIA BIPHASIC ACTUATION" and filed on Jan. 10, 2020, the entire contents of which are incorporated herein by reference.

BACKGROUND

The present disclosure relates to ultrasound transducers and ultrasound transducer arrays. More particularly, the present disclosure relates to the directional control of ultrasound energy.

Many applications of involving ultrasound involve the need to scan an ultrasound beam. For example, many applications in medical ultrasound imaging and medical ultrasound therapy require a scanned ultrasound beam. Conventional approaches to ultrasound beam scanning require either a mechanical scanning mechanism or an electronically-scanned ultrasound array, the former of which can be problematic due to size and mechanical failure modes, and the latter of which can be disadvantageous due to cost and complexity.

SUMMARY

Systems and methods are provided whereby a directional property of an ultrasound transducer element, such as a steering direction, is controlled according to a first driving waveform that is delivered to opposing propagation electrodes and a second driving waveform that is delivered to opposing lateral electrodes. The directional property may be controlled according to a phase difference and/or relative amplitude between the first and second driving waveforms, and/or the selective actuation of one or more lateral electrodes when the lateral electrodes are defined in an array. The ultrasound transducer element may be a ring-shaped transducer element and a directional property associated with a focal region may be controlled. In some example embodiments, array elements of an ultrasound transducer array may each include propagation and lateral electrodes, with each array element being driven by respective first and second driving waveforms to focus the ultrasound energy emitted by the ultrasound transducer array.

Accordingly, in a first aspect, there is provided a method of directionally controlling an ultrasound transducer element, the ultrasound transducer element comprising a piezoelectric material and further comprising a pair of propagation electrodes respectively contacting first opposing surfaces that are perpendicular to a first direction and a pair of lateral electrodes respectively contacting second opposing surfaces that are perpendicular to the first opposing surfaces, the method comprising:

actuating the ultrasound transducer element according to a first driving waveform and a second driving waveform, the first driving waveform and the second driving waveform having a common frequency, such that the first driving waveform is applied to the propagation electrodes and the second driving waveform is applied to the lateral electrodes; and employing at least one of (i) a phase difference between the first driving waveform and the second driving waveform and (ii) an amplitude ratio between the first driving waveform and the second driving waveform, to control a directional property of ultrasound energy emitted by the ultrasound transducer element.

In some example implementations of the method, the first driving waveform and the second driving waveform are controlled according to a predetermined relationship between the directional property of the ultrasound energy emitted by the ultrasound transducer element and one or both of (i) the phase difference between the first driving waveform and the second driving waveform and (ii) the amplitude ratio between the first driving waveform and the second driving waveform. The predetermined relationship may be determined, at least in part, according to ultrasound measurements. The predetermined relationship may be determined, at least in part, according to simulations.

In some example implementations of the method, the second opposing surfaces are a first lateral surface and a second lateral surface, and wherein at least one of the first lateral surface and the second lateral surface has at least one additional lateral electrode provided thereon; and wherein at least one lateral electrode on the first lateral surface and at least one lateral electrode on the second lateral surface are employed to apply the second driving waveform as a potential difference between the first lateral surface and the second lateral surface; and wherein the directional property is controlled, at least in part, by dynamically selecting the lateral electrodes that are employed to apply the potential difference.

In some example implementations of the method, the lateral electrodes comprise a first lateral electrode and a second lateral electrode, and wherein the first lateral electrode and the second lateral electrode have different respective areas.

In some example implementations of the method, the lateral electrodes comprise a first lateral electrode and a second lateral electrode, and wherein the first lateral electrode is spatially offset in the first direction relative to the second lateral electrode.

In some example implementations of the method, the directional property is a steering angle. At least one of (i) the phase difference between the first driving waveform and the second driving waveform and (ii) the amplitude ratio between the first driving waveform and the second driving waveform may be controlled to vary the steering angle. One or both of (i) the phase difference between the first driving waveform and the second driving waveform and (ii) the amplitude ratio between the first driving waveform and the second driving waveform may be selected to maximize the steering angle of the ultrasound energy emitted by the ultrasound transducer element. One or both of (i) the phase difference between the first driving waveform and the second driving waveform and (ii) the amplitude ratio between the first driving waveform and the second driving waveform may be selected to obtain a maximal efficiency at a given steering angle.

In some example implementations of the method, the directional property is a lateral spatial offset of a near-field region of the ultrasound energy.

In some example implementations of the method, the second opposing surfaces are perpendicular to a second direction, and wherein the ultrasound transducer element is further actuated according to a third driving waveform that is applied to the ultrasound transducer element along a third direction that is perpendicular to the first direction and the second direction; and wherein at least one of (i) a phase difference between the first driving waveform and the third driving waveform and (ii) an amplitude ratio between the first driving waveform and the third driving waveform is employed to control the directional property of ultrasound energy emitted by the ultrasound transducer element.

In some example implementations of the method, the ultrasound transducer element has a ring-shaped cross section in a plane perpendicular to the first direction, and wherein the directional property is associated with a focal region. The directional property may be a location of a center of the focal region. The directional property may be a size of the focal region. The directional property may be an intensity of the ultrasound energy within the focal region.

In some example implementations of the method, at least one of (i) the phase difference between the first driving waveform and the second driving waveform and (ii) the amplitude ratio between the first driving waveform and the second driving waveform is controlled to vary the location of the focal region.

In some example implementations of the method, the ultrasound transducer element is an annular ultrasound transducer.

In some example implementations of the method, the method further comprises employing a signal from a cavitation detector as a feedback measure to control cavitation associated with the focal region by varying one or more of (i) the phase difference between the first driving waveform and the second driving waveform and (ii) the amplitude ratio between the first driving waveform and the second driving waveform, to control the directional property of ultrasound energy emitted by the ultrasound transducer element. The cavitation detector may be located within a lumen of the ultrasound transducer element.

In some example implementations of the method, the method further comprises employing a signal from an additional ultrasound transducer to control the directional property of ultrasound energy emitted by the ultrasound transducer element, wherein the additional ultrasound transducer is an imaging ultrasound transducer. The imaging ultrasound transducer may be located within a lumen of the ultrasound transducer element.

In some example implementations of the method, the ultrasound transducer element has a cross section, in a plane perpendicular to the first direction, that forms a segment of a ring.

In some example implementations of the method, the ultrasound transducer element is an ultrasound array element of an ultrasound transducer array. The ultrasound transducer array may be controlled, via transmit beamforming, to focus the ultrasound energy emitted therefrom to a focal region, and wherein the directional property is a steering angle, and wherein the steering angle is selected such that the ultrasound energy emitted by the ultrasound array element is angled, relative to the first direction, toward the focal region. The steering angle may be selected such that the ultrasound energy emitted by the ultrasound array element is directed at the focal region. The focal region may be smaller than a diffraction limited focal region that would be achievable according to unidirectional actuation of the ultrasound transducer element. The ultrasound transducer array may be formed from a set of concentric ultrasound array elements, each concentric ultrasound array element having a ring-shaped cross section in a plane perpendicular to the first direction.

In another aspect, there is provided a method of directionally controlling an ultrasound transducer array, the ultrasound transducer array comprising ultrasound array elements, each ultrasound array element comprising a piezoelectric material, each ultrasound array element further comprising a pair of propagation electrodes respectively contacting first opposing surfaces that are perpendicular to a first direction and a pair of lateral electrodes respectively contacting second opposing surfaces that are perpendicular to the first opposing surfaces, the method comprising:

while performing transmit beamforming with the ultrasound transducer array:
actuating each ultrasound array element of the ultrasound transducer array with a first respective driving waveform and a second respective driving waveform, the first respective driving waveform and the second respective driving waveform having a common frequency, such that the first respective driving waveform is applied to the propagation electrodes and the second respective driving waveform is applied to the lateral electrodes; and
wherein at least one of (i) a respective phase difference between the first respective driving waveform and the second respective driving waveform and (ii) a respective amplitude ratio between the first respective driving waveform and the second respective driving waveform is employed for each ultrasound array element such that ultrasound energy emitted by the ultrasound array elements is focused at a focal region.

In some example implementations of the method, the ultrasound energy is focused at the focal region based on biphasic steering, in the absence of time-of-flight beamforming.

In some example implementations of the method, the ultrasound energy is focused at the focal region based on a combination of biphasic steering and time-of-flight beamforming. The focal region may be smaller than a diffraction limited focal region that would be achievable according to time-of-flight beamforming in an absence of biphasic steering.

In another aspect, there is provided a method of directionally controlling a segmented ring ultrasound transducer, the segmented ring ultrasound transducer comprising a set of ring segments, each ring segment being separated from an adjacent ring segment by a gap, wherein each ring segment comprises a piezoelectric material, and wherein each ring segment further comprises a pair of propagation electrodes respectively contacting first opposing surfaces that are perpendicular to a first direction and a pair of lateral electrodes respectively contacting second opposing surfaces that are perpendicular to the first opposing surfaces, the method comprising:

actuating each ring segment of the segmented ring ultrasound transducer according to a first respective driving waveform and a second respective driving waveform, the first respective driving waveform and the second respective driving waveform having a common frequency, such that the first respective driving waveform is applied to the propagation electrodes and the second respective driving waveform is applied to the lateral electrodes;
wherein at least one of (i) a respective phase difference between the first respective driving waveform and the second respective driving waveform and (ii) a respective amplitude ratio between the first respective driving waveform and the second respective driving waveform, is employed to control a respective directional property of ultrasound energy emitted by each ring segment of the segmented ring ultrasound transducer.

In another aspect, there is provided an ultrasound system comprising:
an ultrasound transducer element comprising a piezoelectric material, the ultrasound transducer element further comprising a pair of propagation electrodes respectively contacting first opposing surfaces that are perpendicular to a first direction and a pair of lateral electrodes respectively contacting second opposing surfaces that are perpendicular to the first opposing surfaces; and
control circuitry operatively coupled to the ultrasound transducer element, the control circuitry comprising at least one processor and associated memory, the memory storing instructions executable by the at least one processor for performing operations comprising:
actuating the ultrasound transducer element according to a first driving waveform and a second driving waveform, the first driving waveform and the second driving waveform having a common frequency, such that the first driving waveform is applied to the propagation electrodes and the second driving waveform is applied to the lateral electrodes; and
controlling a directional property of ultrasound energy emitted by the ultrasound transducer element according to at least one of (i) a phase difference between the first driving waveform and the second driving waveform and (ii) an amplitude ratio between the first driving waveform and the second driving waveform.

In some example implementations of the system, the lateral electrodes comprise a first lateral electrode and a second lateral electrode, wherein the first lateral electrode and the second lateral electrode have different respective areas.

In some example implementations of the system, the lateral electrodes comprise a first lateral electrode and a second lateral electrode, wherein the first lateral electrode is spatially offset in the first direction relative to the second lateral electrode.

In some example implementations of the system, the system further comprises a cavitation detector, wherein the control circuitry is configured to employ a signal from the cavitation detector as a feedback measure to control cavitation associated with the focal region by varying one or more of (i) the phase difference between the first driving waveform and the second driving waveform and (ii) the amplitude ratio between the first driving waveform and the second driving waveform, to control the directional property of ultrasound energy emitted by the ultrasound transducer element. The cavitation detector may be located within a lumen of the ultrasound transducer element.

In some example implementations of the system, the system further comprises an additional ultrasound transducer, wherein the additional ultrasound transducer is an imaging ultrasound transducer, and wherein the control circuitry is configured to employ a signal from the additional ultrasound transducer to control the directional property of ultrasound energy emitted by the ultrasound transducer element. The imaging ultrasound transducer may be located within a lumen of the ultrasound transducer element.

In some example implementations of the system, the second opposing surfaces are a first lateral surface and a second lateral surface, and wherein at least one of the first lateral surface and the second lateral surface has at least one additional lateral electrode provided thereon; and wherein the control circuitry is configured such that at least one lateral electrode on the first lateral surface and at least one lateral electrode on the second lateral surface are employed to apply the second driving waveform as a potential difference between the first lateral surface and the second lateral surface; and wherein the control circuitry is further configured such that the directional property is controlled, at least in part, by dynamically selecting the lateral electrodes that are employed to apply the potential difference.

In another aspect, there is provided an ultrasound system comprising:
an ultrasound transducer array, the ultrasound transducer array comprising ultrasound array elements, each ultrasound array element comprising a piezoelectric material, each ultrasound array element further comprising a pair of propagation electrodes respectively contacting first opposing surfaces that are perpendicular to a first direction and a pair of lateral electrodes respectively contacting second opposing surfaces that are perpendicular to the first opposing surfaces; and
control circuitry operatively coupled to the ultrasound transducer array, the control circuitry comprising at least one processor and associated memory, the memory storing instructions executable by the at least one processor for performing operations comprising:
while performing transmit beamforming with the ultrasound transducer array:
actuating at least one ultrasound array element with a first respective driving waveform and a second respective driving waveform, the first respective driving waveform and the second respective driving waveform having a common frequency, such that the first respective driving waveform is applied to the propagation electrodes and the second respective driving waveform is applied to the lateral electrodes; and
wherein at least one of (i) a respective phase difference between the first respective driving waveform and the second respective driving waveform and (ii) a respective amplitude ratio between the first respective driving waveform and the second respective driving waveform is employed to control a respective directional property of ultrasound energy emitted by the at least one ultrasound array element.

In another aspect, there is provided a segmented ring ultrasound transducer comprising:
a set of ring segments, each ring segment being separated from an adjacent ring segment by a gap, wherein each ring segment comprises a piezoelectric material;
each ring segment further comprising a pair of propagation electrodes respectively contacting first opposing surfaces that are perpendicular to a first direction and a pair of lateral electrodes respectively contacting second opposing surfaces that are perpendicular to the first opposing surfaces.

In some example implementations, the segmented ring ultrasound transducer further comprises a cavitation detector, wherein the cavitation detector is surrounded by the set of ring segments.

In some example implementations, the segmented ring ultrasound transducer further comprises an imaging ultrasound transducer, wherein the imaging ultrasound transducer is surrounded by the set of ring segments.

In another aspect, there is provided a method of directionally controlling an ultrasound transducer element, the ultrasound transducer element comprising a piezoelectric material and further comprising a pair of propagation respectively electrodes respectively contacting first opposing surfaces that are perpendicular to a first direction and a pair of lateral electrodes respectively contacting second opposing surfaces that are perpendicular to the first opposing surfaces, wherein the second opposing surfaces are a first lateral surface and a second lateral surface, and wherein at least one of the first lateral surface and the second lateral surface has at least one additional lateral electrode provided thereon, the method comprising:

actuating the ultrasound transducer element according to a first driving waveform and a second driving waveform, the first driving waveform and the second driving waveform having a common frequency, such that the first driving waveform is applied to the propagation electrodes, and such that at least one lateral electrode on the first lateral surface and at least one lateral electrode on the second lateral surface are employed to apply the second driving waveform as a potential difference between the first lateral surface and the second lateral surface; and controlling a directional property of ultrasound energy emitted by the ultrasound transducer element, at least in part, by dynamically selecting the lateral electrodes that are employed to apply the potential difference.

In another aspect, there is provided an ultrasound system comprising:

an ultrasound transducer element comprising a piezoelectric material, the ultrasound transducer element further comprising a pair of propagation electrodes respectively contacting first opposing surfaces that are perpendicular to a first direction and a pair of lateral electrodes respectively contacting second opposing surfaces that are perpendicular to the first opposing surfaces, wherein the second opposing surfaces are a first lateral surface and a second lateral surface, and wherein at least one of the first lateral surface and the second lateral surface has at least one additional lateral electrode provided thereon; and control circuitry operatively coupled to the ultrasound transducer element, the control circuitry comprising at least one processor and associated memory, the memory storing instructions executable by the at least one processor for performing operations comprising:

actuating the ultrasound transducer element according to a first driving waveform and a second driving waveform, the first driving waveform and the second driving waveform having a common frequency, such that the first driving waveform is applied to the propagation electrodes, and such that at least one lateral electrode on the first lateral surface and at least one lateral electrode on the second lateral surface are employed to apply the second driving waveform as a potential difference between the first lateral surface and the second lateral surface; and controlling a directional property of ultrasound energy emitted by the ultrasound transducer element, at least in part, by dynamically selecting the lateral electrodes that are employed to apply the potential difference.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIGS. 12A and 12B plot maximum positive and negative steering produced by the FEA transducer model on the left and right direction while applying 1 W on both sets of electrodes at biaxial phases of 90° and 315°.

FIGS. 12C and 12D demonstrate steering, in both directions, as measured on the single element biaxial transducer B1 with the same power as in the FEA model, also with biaxial phases of 90° and 315°.

FIGS. 13A-13C plot finite-element (ANSYS 19.2) simulations of the acoustic field (dB scale) in biaxial prismatic transducer operating at 133 kHz where steering (α) of ultrasound appears modified in function of the de-phase angle (ϕ); 1 W was applied on the propagation direction and 1 W on the lateral direction (energy ratio, $E_R$=1). Three difference case of simulation are shown: (A) without biaxial driving (Only-P), which is standard driving method where the beam is generated "straight" up in the sound propagation (Z); (B) with biaxial driving having a dephase angle of 90° (FEA Model ϕ=90°) showing steering towards the left of the transducer); and (C) with biaxial driving having a dephase angle of 315° (FEA Model ϕ=315°) showing steering towards the right of the transducer.

FIGS. 16A-16E plot the dependence of efficiency on phase for various configurations, presenting results of η vs. ϕ for each of the three experimental biaxial transducers (FIG. 16A for $B_1$, FIG. 16B for $B_2$ and FIG. 16C for $B_3$) for different values of $p_l$. The results of the average η for the three conventional transducers is also shown for comparison. Average η vs. ϕ is also plotted for the three biaxial transducers (FIG. 16D) and corresponding FEA predictions for η vs. ϕ for the same values of $p_l$ (FIG. 16E).

FIGS. 18A-18E show (A) a schematic of a 3-element biaxial phased-array, and (B-E) FEA acoustic field measurements (dB scale) when the transducer is driven with different methods. The "+" symbol shows the center of the −6 dB contour, showing (B) traditional driving mode and no focusing; (C) traditional driving mode+TOF focusing; (D) Biaxial steering alone; and (E) Biaxial+TOF focusing.

FIG. 26A shows a single-element (1D) imaging transducer, FIG. 26B shows a linear array (2D) imaging transducer, and FIG. 26C shows a 2D array (3D) imaging transducer.

DETAILED DESCRIPTION

Figure 1A:
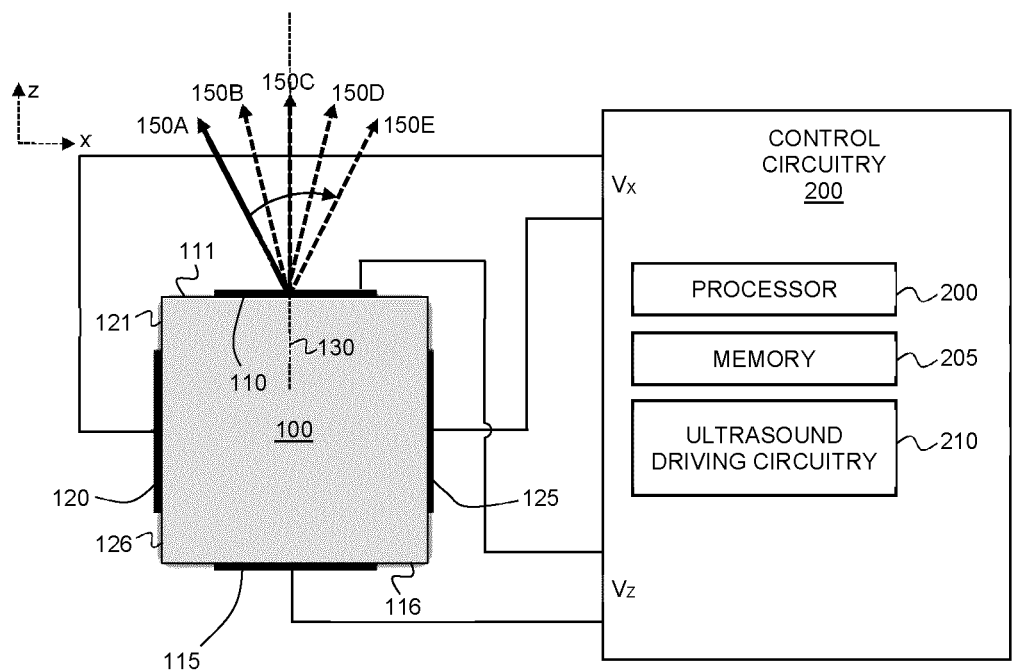
FIGS. 1A-1C show (A) an example biphasic ultrasound transducer system for controlling the directional properties of ultrasound energy emitted by an ultrasound transducer element, (B) an example phase difference between the first and second biphasic driving waveforms applied to the propagation and lateral electrodes, respectively, and (C) an example method for controlling the directional properties of ultrasound energy emitted by an ultrasound transducer element.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

As used herein, the phrase "prismatic ultrasound transducer element" refers to an ultrasound transducer element having a three-dimensional shape characterized by a first pair of opposing parallel planar sides and at least one additional pair of opposing parallel planar sides, where the first pair of opposing parallel planar sides are orthogonal to the at least one additional pair of opposing parallel planar sides. Non-liming examples of prismatic ultrasound transducers include ultrasound transducer elements shaped in the form of a cube or a rectangular prism.

In International Patent Application No. PCT/CA2014/051113, titled "Methods of Driving Polarization Inversion in Ferroelectric Materials and Devices", filed on Nov. 21, 2014, which is incorporated herein by reference in its entirety, Rubel et al. recognized that the energy diagram of ferroelectric perovskite oxides exhibits strong anisotropy in the coercive field, and that this anisotropy can be employed to produce polarization inversion with a reduced applied coercive voltage or bias. In particular, it was disclosed that a uniaxial method of driving the central ion through the central maxima of the anisotropic potential energy surface represents only one of a multitude of possible transition paths, and this path is not an energetically favorable path. Rubel et al. demonstrated both the uniaxial path and also an alternative, lower energy path that involves the application of a reduced coercive field (and associated applied bias).

Rubel et al. described how the anisotropy in the potential energy surface can be employed to produce methods of driving polarization inversion (e.g. switching) in a ferroelectric material with a reduced coercive field relative to uniaxial excitation, where the ferroelectric material possess an anisotropic potential energy surface having an energy barrier for a curved switching path that is lower than for the barrier for a direct path associated with uniaxial switching. Rubel et al. explained how polarization inversion with reduced coercivity could be obtained via the application of an electric field that exhibits a time-dependent orientation, in contrast with conventional uniaxial electrical excitation, thereby causing the central ion (and the crystal structure as a whole) to evolve along a lower-energy path in which the central ion is driven such that it avoids the potential energy maximum.

Rubel et al. described the use of biphasic excitation of an ultrasound transducer element, in which non-parallel time-dependent voltages (e.g. bias, potential) are applied such that the direction of the electric field changes with during the switching cycle. Rubel et al. described the application of biphasic voltages to two pairs of orthogonally-positioned electrodes, with a phase difference applied therebetween, in order to effect polarization inversion with a reduced coercive field.

As disclosed in International Patent Application No. PCT/CA2014/051113, it was previously believed that the biphasic effect was applicable only for the excitation of an ultrasound transducer in order to achieve more efficient excitation of ultrasound energy. While the biphasic driving method employed by Rubel et al. in International Patent Application No. PCT/CA2014/051113 was described as facilitating an increase in emitted ultrasound energy and efficiency, the present inventors have discovered that the phase difference between the biphasic driving signals and/or the amplitude of the biphasic driving signals can be employed to control one or more directional properties of the ultrasound energy emitted by an ultrasound transducer element. As described in detail below, and as shown in the examples below, the present inventors have discovered that when biphasic actuation signals are applied to an ultrasound transducer element, biphasic driving is not only beneficial in improving the efficiency of emitting ultrasound energy, but it also useful for controlling directional properties of the emitted ultrasound energy. Remarkably, as demonstrated herein, biphasic driving is shown to facilitate directional steering of ultrasound energy emitted from a single ultrasound transducer element, in stark contrast to conventional steering methods that rely on either mechanical single-element steering or phased-array steering of multiple transducer elements.

Accordingly, in various example embodiments of the present disclosure, systems and methods are provided in which biphasic excitation of an ultrasound transducer element is employed to control a directional property of the emitted ultrasound energy. For example, in the case of a prismatic ultrasound transducer, biphasic electrical excitation (i.e. electrical actuation, electrical driving) may be employed to control (e.g. prescribe or steer) the direction of the emitted ultrasound energy, or to control the lateral offset of a near field region of the emitted ultrasound energy. Furthermore, in the example case of an ultrasound transducer element having a ring-shaped cross-section, such as an annular transducer, biphasic excitation may be employed to control the location and/or size of the focal region associated with the emitted ultrasound energy.

Indeed, as shown in the Examples below, the present example biphasic directional control methods may be employed for applications including, but not limited to: (i) facilitating steering of single ultrasound transducer elements, (ii) controlling the lateral spatial offset of the near field ultrasound energy in a single-element ultrasound transducer, (iii) improving the focusing of phased-array ultrasound transducer arrays beyond that which is achievable using time-of-flight beamforming, and (iv) controlling the axial location and/or size of a focal region associated with a ring-shaped ultrasound transducer. Such example implementations, and other implementations of the present example systems and methods, may be beneficial in applications including, but not limited to, therapeutic ultrasound, ultrasound imaging, and ultrasound sensors.

Referring now to FIG. 1A, an example system and method is shown for controlling the directional emission of ultrasound energy from an ultrasound transducer element. The ultrasound transducer element 100 is formed from a piezoelectric material that is poled along a direction parallel to axis 130 and includes propagation electrodes (110, 115) that contact respective opposing first surfaces (111 116), and lateral electrodes (120, 125) that contact respective second opposing surfaces (121, 126) which are perpendicular to the first opposing surfaces (111, 116). The ultrasound transducer element 100 is actuated by a first driving waveform ($V_z$, applied as a potential difference between the propagation electrodes) and a second driving waveform ($V_x$, applied as a potential difference between the lateral electrodes) that have a common frequency, with the first driving waveform being applied to the propagation electrodes and the second driving waveform being applied to the lateral electrodes, such that ultrasound energy is emitted through the surface 111.

Figure 1B:
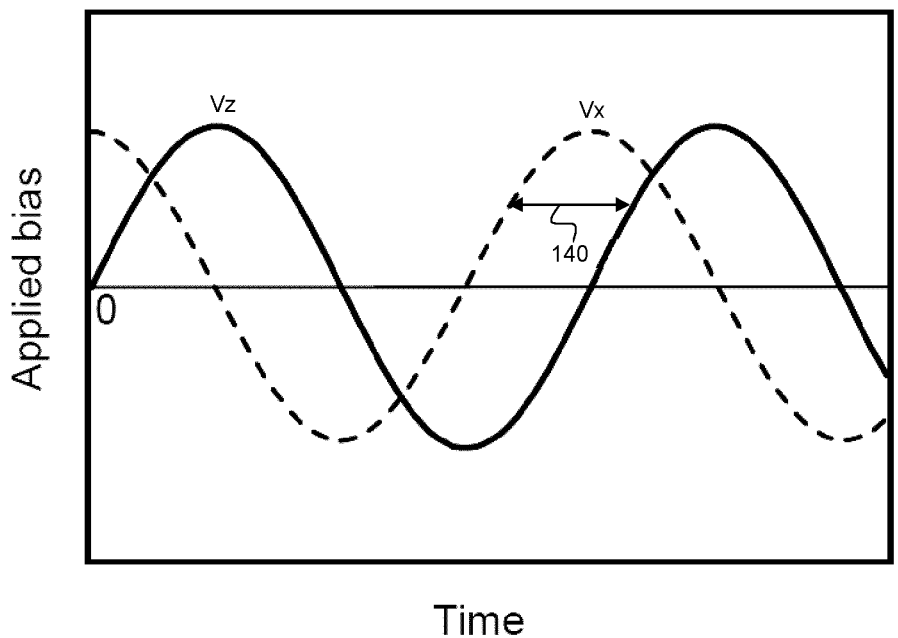

As noted above, the present inventors have discovered that the ultrasound emission direction (150A-150E in FIG. 1A) is dependent on the phase difference between the first driving waveform and the second driving waveform. Accordingly, in some example implementations, the emission direction of the ultrasound energy may be selected by employing a suitable value of the phase difference between the first and second driving waveforms. An example of a phase difference for achieving biphasic steering is shown in FIG. 1B. As shown in FIG. 1A, steering can be achieved in a plane that is perpendicular to the plane of the propagation electrodes and the plane of the lateral electrodes.

The present inventors have also discovered that the ultrasound emission direction is dependent on the relative amplitudes of the first and second driving waveforms. Therefore, even though FIG. 1B illustrates an example case in which the first and second waveforms have a common amplitude, it will be understood that the relative amplitudes need not be equal, and that control over the emission direction of the emitted ultrasound energy may controlled, in addition or in alternative to the aforementioned method involving the phase difference, by varying the relative amplitude of the first and second driving waveforms.

Figures 14, 15:
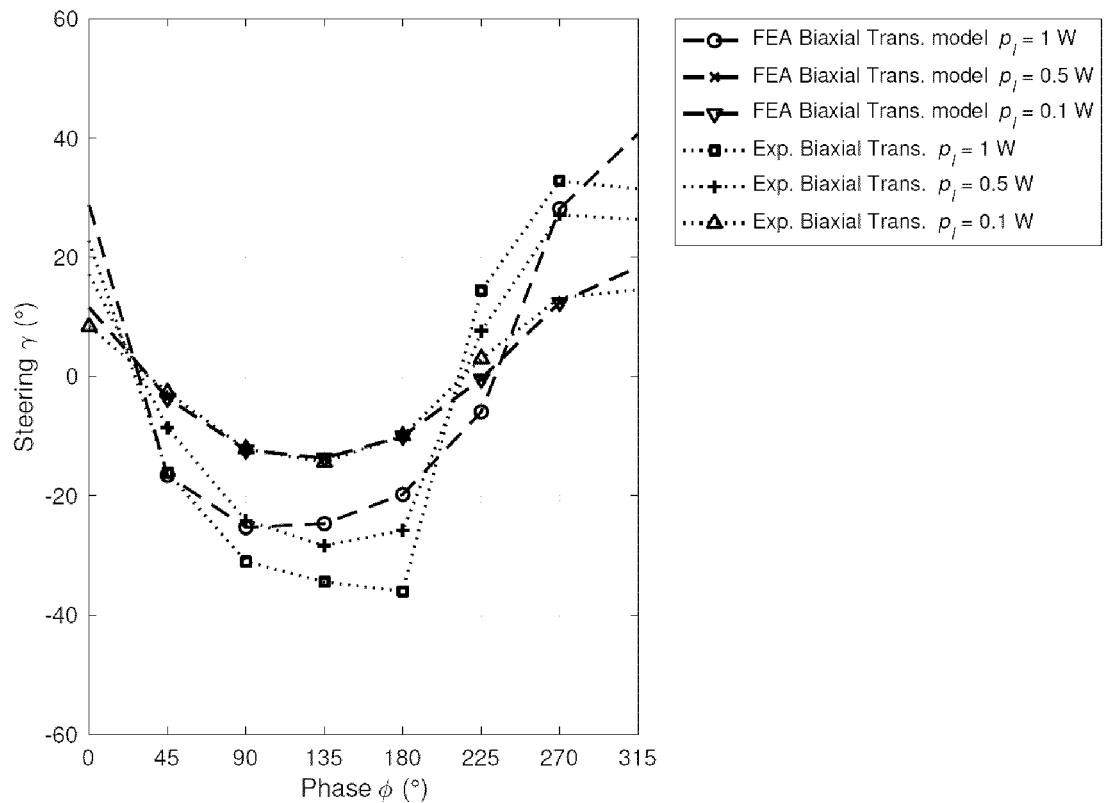
FIG. 14 plots the steering response as a function of the difference in phase for the FEA transducer model and three experimental biaxial transducers (average) at different powers applied on the lateral electrode.
FIG. 15 is a table summarizing maximal steering angles observed with the FEA predictions and obtained from experimental measurements (n=3).

The dependence of a biaxially-driven ultrasound transducer element on the phase difference between the first and second driving waveforms (applied to the propagation and lateral electrodes) is investigated, both experimentally (using fabricated ultrasound transducer elements) and computationally (using finite element simulations), in the Examples section provided below. The present inventors observed that in the example case of a prismatic ultrasound transducer element having a shape in the form of a rectangular prism, the steering angle of the emitted ultrasound beam exhibits a sinusoidal dependence on the phase difference between the first and second driving waveforms, as shown in FIG. 14.

Moreover, the steering angle was also found to be dependent on the relative amplitudes of the first and second driving waveforms, with higher steering angles being achievable for cases in which the amplitudes of the first and second driving waveforms were similar. Notably, the angular ranges corresponding to the maximum steering angles (in either direction) did not depend significantly on the relative amplitudes of the first and second driving waveforms, with the relative amplitudes of the waveforms effectively multiplicatively scaling the steering angle curve.

Figure 1C:
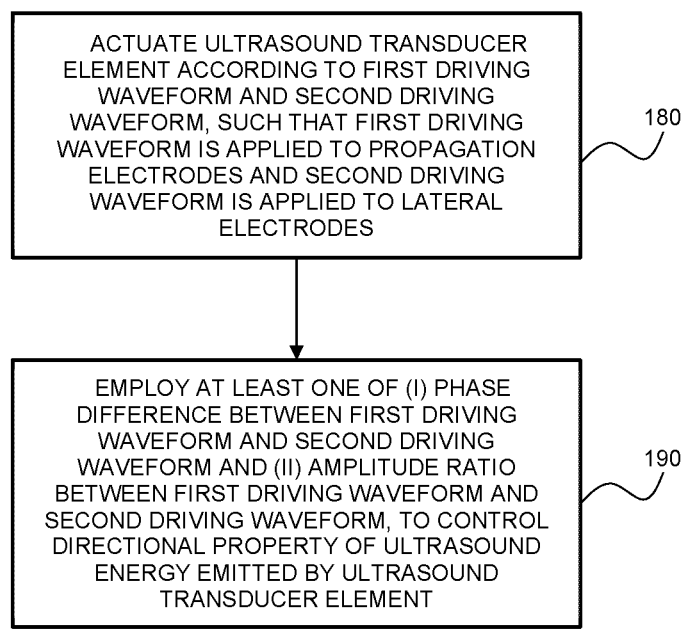

FIG. 1C is a flow chart that illustrates, via example steps 180 and 190, a method of controlling a directional property of an ultrasound transducer element using control of one or more of (i) a phase difference between the first and second driving waveforms and (ii) a relative amplitude between the first and second driving waveforms. In some example implementations, a pre-determined relationship between the biphasic phase difference and the direction of emitted ultrasound energy may be employed to control ultrasound transducer element such that ultrasound energy is emitted by the ultrasound transducer element along a selected direction. For example, a look-up table may be employed (e.g. with interpolation) to determine a suitable phase difference (between the first and second driving signals) in order to achieve ultrasound emission along the selected direction (i.e. such that a beam axis corresponding to a maximal intensity of the emitted ultrasound is aligned along the selected direction), or such that the emission efficiency is maximized at a given steering angle.

The pre-determined relationship may be determined, at least in part, empirically or experimentally, for example, via measurements made with a specific ultrasound transducer or averaged over measurements made using multiple ultrasound transducers). Alternatively, the pre-determined relationship may be established, as least in part, via simulations. In some example implementations, the pre-determined relationship may be established between the direction of emitted ultrasound energy and both (i) the biphasic phase difference between the first and second driving waveforms and (ii) the relative amplitudes of the first and second driving waveforms. It will be understood that the relationship between a given directional property and one or more of the phase difference and the relative amplitude of the biphasic driving waveforms may depend on the geometrical and material properties of the ultrasound transducer element, and that the relationship may be investigated experimentally and/or computationally for a given transducer geometry and material choice.

As demonstrated in FIGS. 16A-16E, the efficiency of ultrasound emission was also found to be dependent on both the phase difference and the relative amplitudes of the first and second driving waveforms. In particular, it was found that greater emission efficiency could be achieved when the amplitude of the first driving waveform (applied to the propagation electrodes) exceeded the amplitude of the second driving waveform (applied to the lateral electrodes). Accordingly, it may be beneficial to employ driving conditions (i.e. a selected phase difference and relative amplitudes of the first and second driving waveforms) that balance competing constraints involving steering angle and emission efficiency.

As can be seen in the Examples provided below, for example, in the acoustic field plots shown in FIGS. 12A-12D and in FIGS. 13B and 13C, the present inventors also discovered that the near-field region of the emitted ultrasound energy is laterally shifted as the phase difference between the first and second driving waveforms is varied. Accordingly, in some example implementations, the biphasic phase difference between the first and second driving waveforms may be employed to control the lateral offset of the near-field region of the emitted ultrasound energy. Such control over the near-field region may find application in near-field imaging, therapy and sensing applications.

It is expected that the biaxial driving methods disclosed herein are applicable to piezoelectric materials including, but not limited to, lead zirconate titanate (PZT) lead titanate (PT), barium titanate (BT) and lead metaniobate.

In many example implementations described herein, the lateral electrodes are shown in a perpendicular configuration relative to the propagation electrodes, and covering most of the surface area of the transducer face. However, it will be understood that the two pairs of electrodes need not be strictly perpendicular or orthogonal. In some example implementations, the pairs of electrodes may be oriented with slight variations relative to a perpendicular configuration, for example, with at 90±5 degrees relative to one another. Also, the pattern of electrodes may not be strictly covering most of the surface area of a transducer face, but only different portions, in such way the electric field that is applied in the lateral electrodes produces a different control of the steering. Also, as described in further detail below, the lateral electrodes can be arranged in an array configuration where individual lateral electrodes can be selectively activated (actuated; for example, using electronic switches) to vary the internal electric field and thus control the steering of the emitted ultrasound energy.

Referring again to FIG. 1A, the first and second driving waveforms, and their relative phase differences and amplitudes, may be controlled via control circuity 200. FIG. 1A schematically illustrates an example of control circuitry that includes one or more processors 200 and memory 205 that is operatively associated with the one or more processors 200. The one or more processors 200 may process instructions stored in the memory 205 to control the ultrasound driving circuitry (e.g. a voltage source, optionally with one or more amplifiers, that generates the two voltage outputs $V_x$ and $V_z$ with controllable relative phases and/or relative amplitudes). The memory 205 may store a pre-determined relationship between the direction of the emitted ultrasound energy and one or both of the biphasic phase difference and the relative amplitudes of the biphasic driving signals, such that the first and second driving signals may be configured according to a selected emission direction (angle) or a selected range of scanning directions (scanning angles). For example, in some example embodiments, one or more of the phase difference and the relative amplitudes of the first and second driving waveforms may be controlled to scan the emitted ultrasound energy among a plurality of directions. For example, the emitted ultrasound energy may be scanned among a plurality of directions, such as directions 150A-150E as shown in FIG. 1A. In some example embodiments, the phase relationship between the biphasic waveforms may be established by an external trigger.

In some example implementations, an additional pair of lateral electrodes may be provided on an additional set of opposing surfaces that reside perpendicular to the propagation electrodes and the first pair of lateral electrodes, and a third driving waveform may be delivered to the additional set of lateral electrodes. One or more of the phase and amplitude of the third waveform may be controlled relative to those of the first driving waveform (or the second driving waveform) in order to achieve beam steering in two dimensions.

While the preceding embodiments have been described within the context of prismatic ultrasound transducer elements, it will be understood that the preceding example methods may be implemented according to other transducer geometries. For example, an ultrasound transducer element having a ring-shaped cross section, such as the annular transducer 250 illustrated in FIG. 2A, formed from a piezoelectric material poled in a direction parallel to a longitudinal axis of the transducer, may be driven according to biphasic driving signals for control over a directional property of the emitted ultrasound energy. For example, propagation electrodes may be provided that contact the top (260) and bottom (not shown) surfaces, and lateral electrodes may be provided that contact the outer 270 and inner 280 lateral surfaces.

Figure 20A:
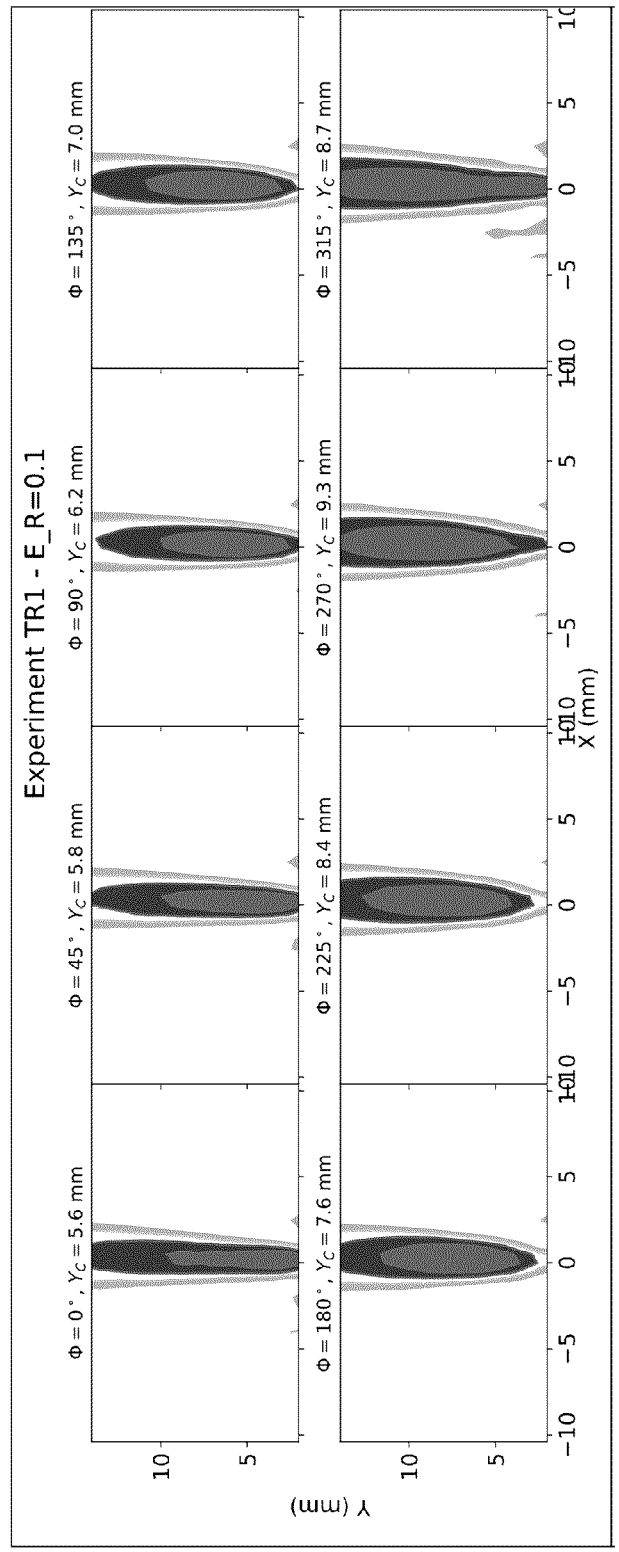
FIGS. 20A and 20B plot experimental 2D acoustic field distributions (normalized dB scale) produced by biaxial ring transducer TR1 operating at 500 kHz for different driving conditions of de-phase and energy level applied on the lateral electrodes. Each subgroup of plots shows results for de-phase angle varied from 0° to 315° in steps of 45°. Results organized for energy ratios $E_R$ 0.1 (FIG. 20A), and 1 (FIG. 20B) on the lateral electrode.
Figure 20B:
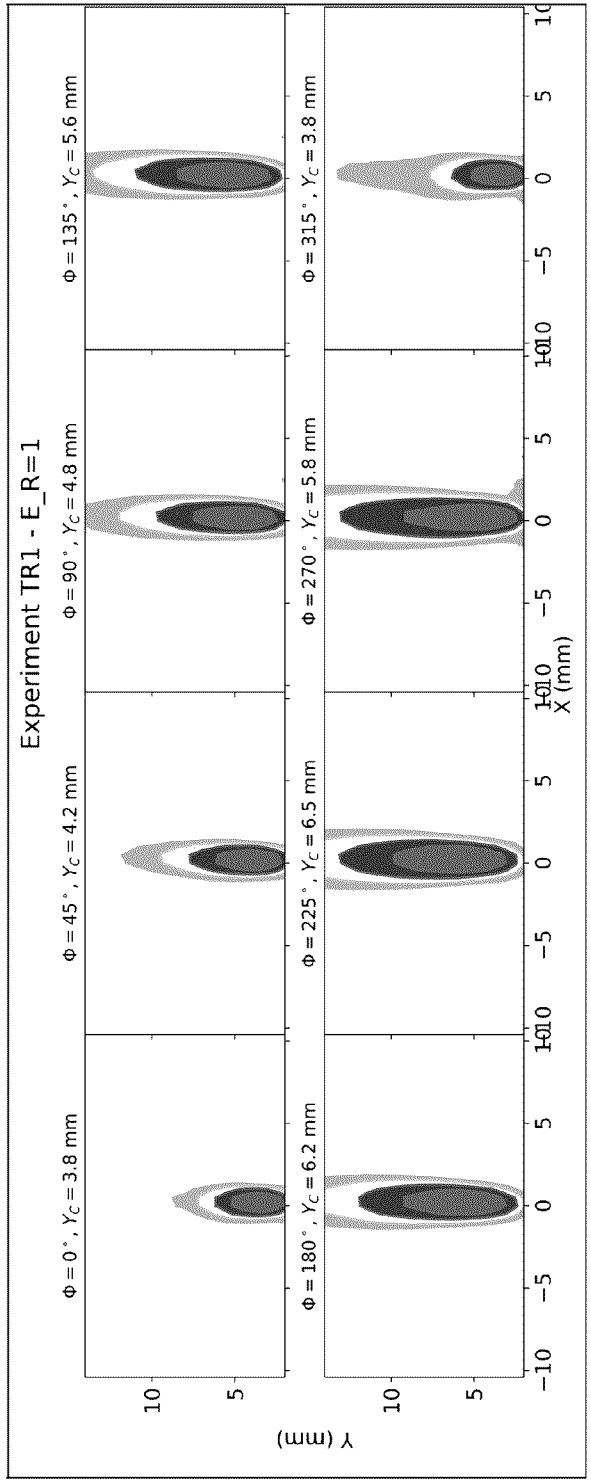
Figure 20C:
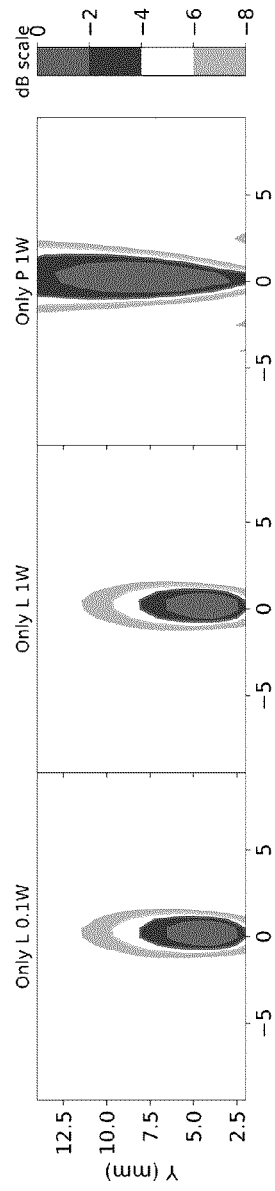
FIG. 20C plots experimental 2D acoustic field distributions (normalized dB scale) produced by biaxial ring transducer TR1 operating at 500 kHz driven only by the lateral electrode (left and center) and the propagation electrode (right). Lateral electrode was driven with 0.1 W (left) and 1 W (center). The test involving driving with the propagation electrodes employed a driving power of 1 W.

As shown in FIGS. 20A-20C, the present inventors have found that when a ring-shaped ultrasound transducer element is driven with biphasic waveforms, with a first waveform being applied to the propagation electrodes and a second waveform being applied to the lateral electrodes, one or more properties of the focal region of the emitted ultrasound energy may be controlled according to at least one of (i) the phase difference between the first and second driving waveforms, and (ii) the relative amplitude between the first and second driving waveforms. For example, as can be seen in FIGS. 20A and 20B, the longitudinal extent of the focal region, the location of the center of the focal region along the transducer axis, and the intensity of the emitted ultrasound energy within the focal region, vary with the applied phase difference and amplitude ratio of the biphasic driving waveforms.

Figure 2A:
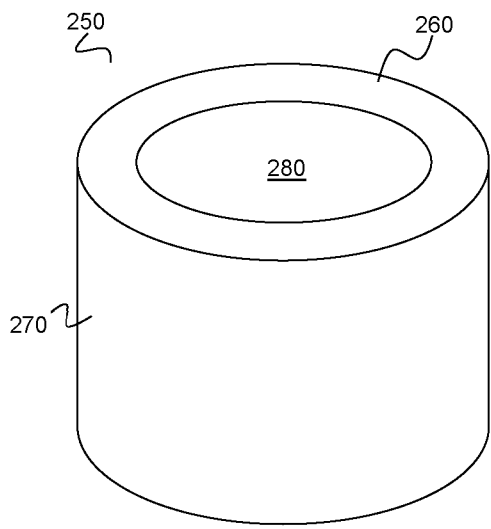
FIGS. 2A-2D illustrate example embodiments in which the ultrasound transducer element controlled with the biphasic driving waveforms has a ring-shaped cross-section.

While FIG. 2A illustrates an example case in which the ring-shaped ultrasound transducer is an annular transducer having a circular cross-sectional shape, it will be understood that the ring-shape need not be circular (for example, the cross-sectional shape can be elliptical or multi-faceted).

Figure 2B:
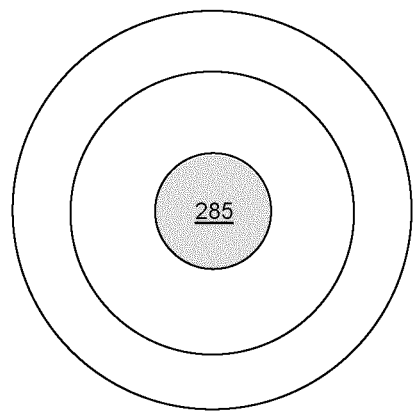

In some example implementations involving a ring-shaped ultrasound transducer element, a sensor or imaging device 285 may be provided within an inner lumen of the ultrasound transducer, as shown in the overhead view presented in FIG. 2B. Non-limiting examples of sensors include an ultrasound imaging transducer that can be used for imaging (both in transmission-reception, or only reception) or an optical sensor. In some example implementations, the sensor 285 can capture a cavitation sensing signal and may be employed as a feedback measure to the control circuitry that is employed to generate the biphasic driving waveforms, and one or more properties of the biphasic waveforms, such as the phase difference or the relative amplitudes of the driving waveforms, may be varied based on the feedback measure, for example, to increase or decrease a level of cavitation, or to induce or suppress cavitation. In alternative example embodiments, the sensor 285 may an optical imaging camera for $Ca^{+2}$ imaging or optogenetics.

Figure 26A:
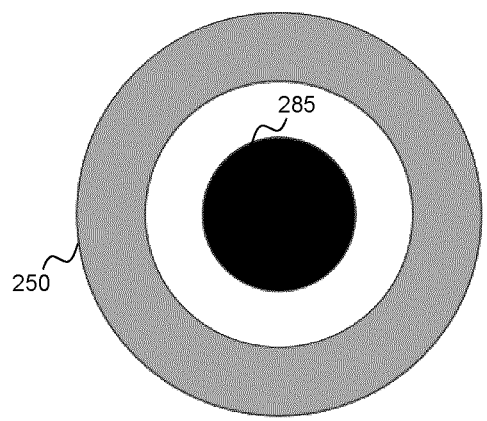
FIGS. 26A-26C show top views of example embodiments that include a biphasic ultrasound ring transducer and additional imaging transducer, where
Figure 26B:
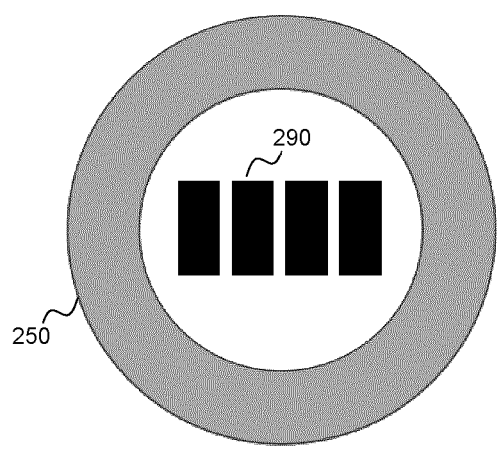
Figure 26C:
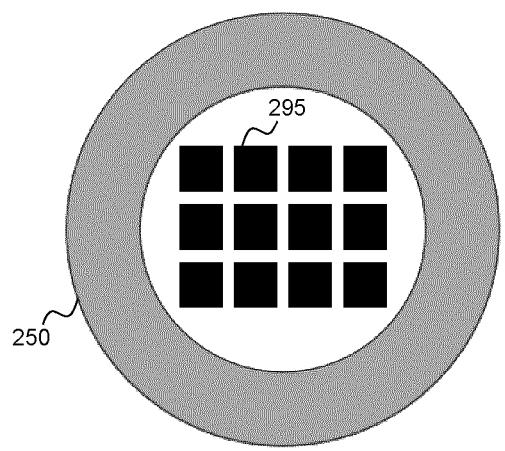

In alternative example embodiments, one or more ultrasound imaging devices can be used in transmission-reception mode to visualize the region being covered by the ultrasound generated by the ring transducer. FIGS. 26A-26C how top views of example embodiments that include a biphasic ultrasound ring transducer and additional imaging transducer, where FIG. 26A shows a single-element (1D) imaging transducer, FIG. 26B shows a linear array (2D) imaging transducer, and FIG. 26C shows a 2D array (3D) imaging transducer.

Figure 2C:
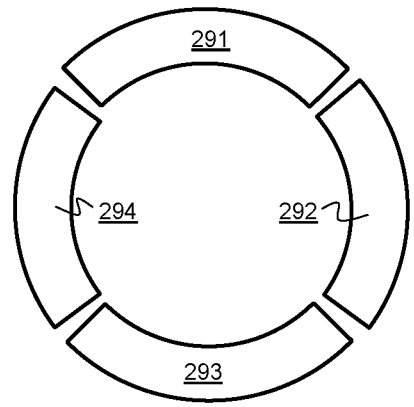
Figure 2D:
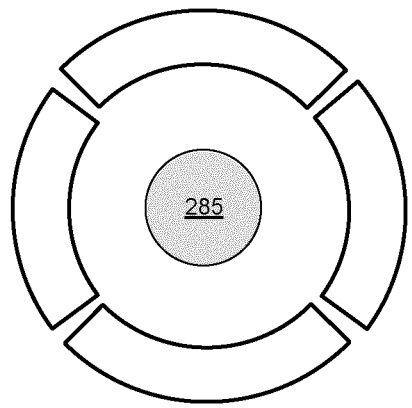

In some example embodiments, a ring-shaped ultrasound transducer may be provided as a plurality of ring segments, as shown in the overhead view presented in FIG. 2C. The figure shows an example implementation involving four segments 291-294, although other example implementations may include a greater or lesser number of segments. According to the present example embodiment, each ring segment includes a distinct set of propagation electrodes and lateral electrodes and therefore functions as a separate element of the ring-shaped ultrasound element, and can be independently actuated and controlled relative to the other ring segments. As each segment is geometrically shaped as a prism, it can be employed to steer the emitted ultrasound energy, as per the preceding embodiments. According, a segmented ring-shaped ultrasound transducer having ring segments driven by per-segment biphasic driving waveforms may be employed to steer the emitted ultrasound beam in one or more directions, in addition to controlling one or more properties of the focal region of the overall emitted ultrasound energy. FIG. 2D illustrates the example case in which the ring segments of the segmented ring ultrasound transducer surround a cavitation sensor or an ultrasound imaging transducer.

While many of the preceding example embodiments employ symmetric lateral electrode configurations in which lateral electrodes on opposing lateral surfaces have a common area and/or a common height or spatial alignment in the propagation direction, the present inventors have found that the directional properties of the ultrasound energy emitted by a biphasic ultrasound transducer can be modified by controlling the relative size and/or spacing of lateral electrodes.

Figure 21A:
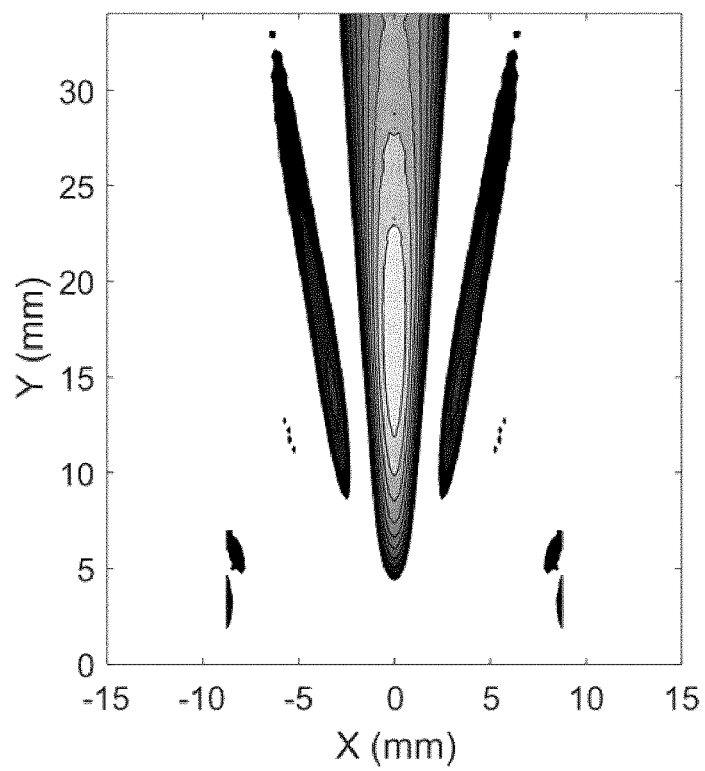
FIGS. 21A and 21B show, respectively, the acoustic field distribution from a ring transducer driven in biaxial mode and a side cross-sectional view of the ring transducer, where the ring transducer has lateral electrodes that are spatially aligned in the propagation direction.
Figure 21B:
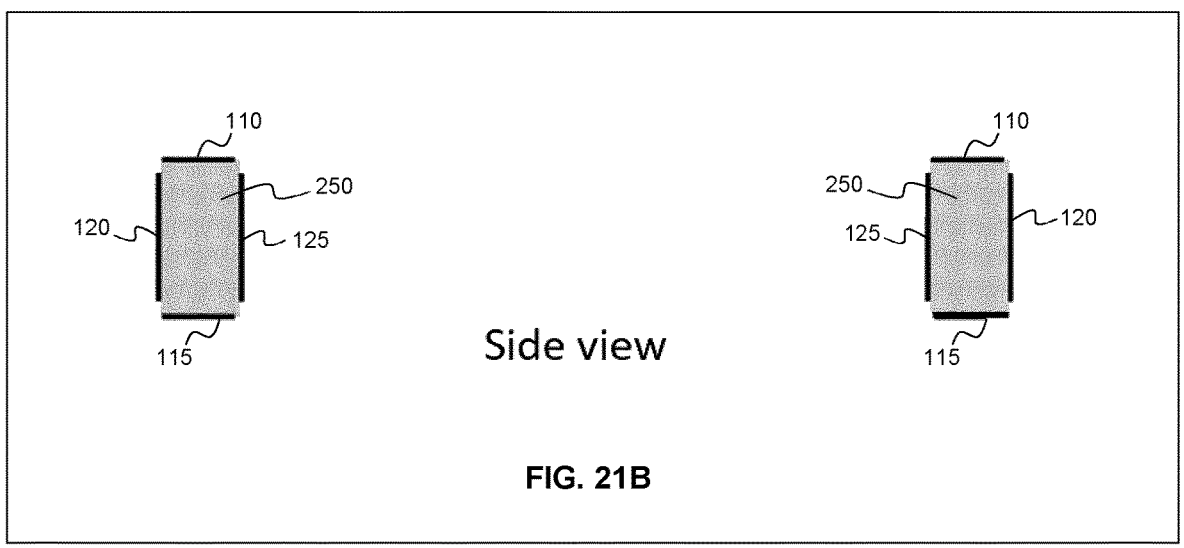
Figure 22A:
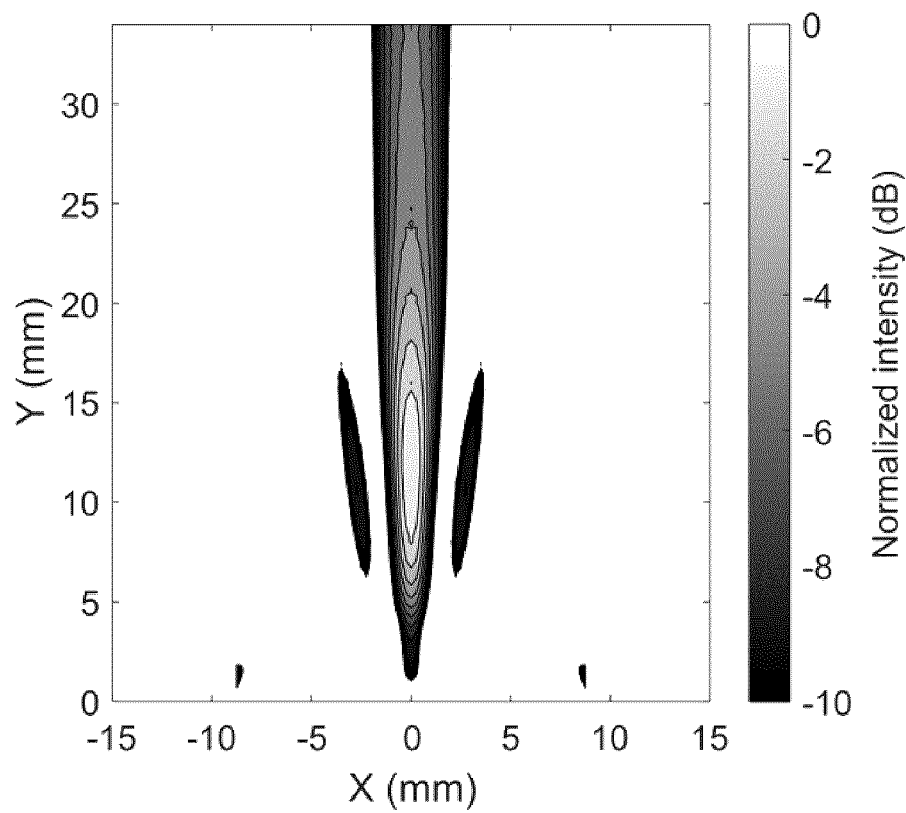
FIGS. 22A and 22B show, respectively, the acoustic field distribution from a ring transducer driven in biaxial mode and a side cross-sectional view of the ring transducer, where the ring transducer has lateral electrodes that are spatially offset in the propagation direction.
Figure 22B:
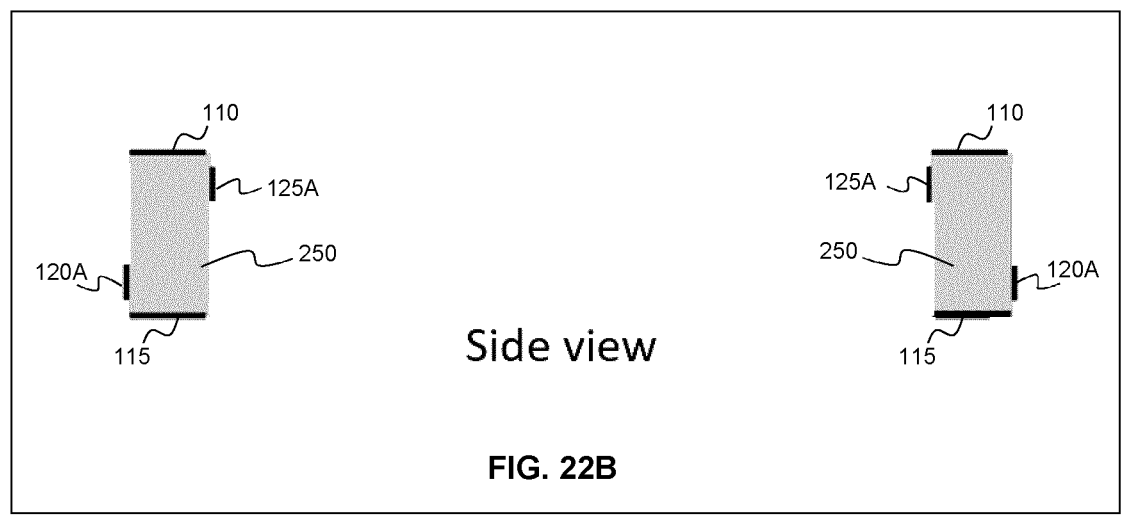
Figure 23A:
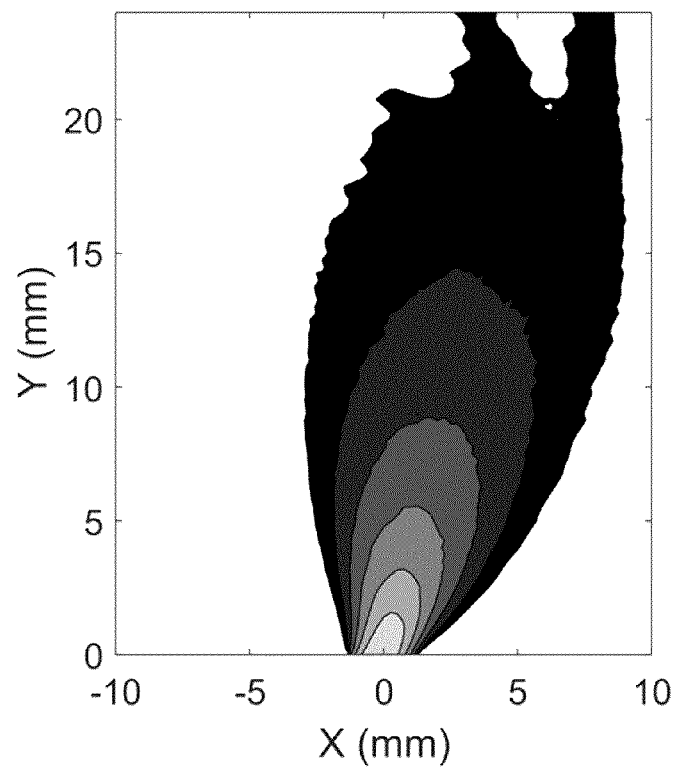
FIGS. 23A and 23B show, respectively, the acoustic field distribution from a prismatic transducer driven in biaxial mode and a side cross-sectional view of the prismatic transducer, where the prismatic transducer has lateral electrodes that are spatially aligned in the propagation direction.
Figure 23B:
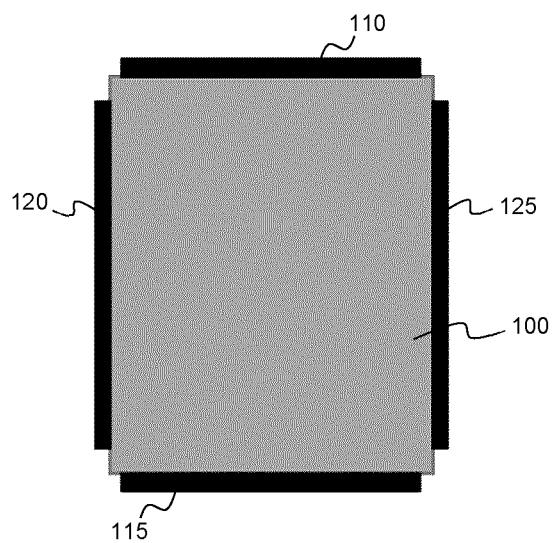
Figure 24A:
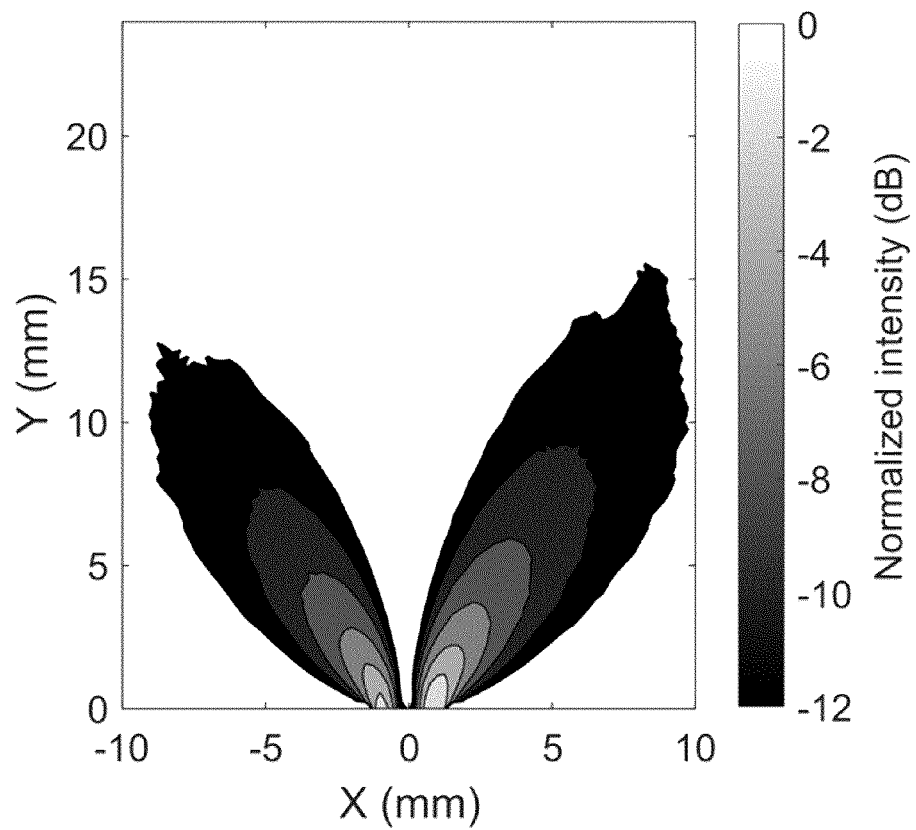
FIGS. 24A and 24B show, respectively, the acoustic field distribution from a prismatic transducer driven in biaxial mode and a side cross-sectional view of the prismatic transducer, where the prismatic transducer has lateral electrodes that are spatially offset in the propagation direction.
Figure 24B:
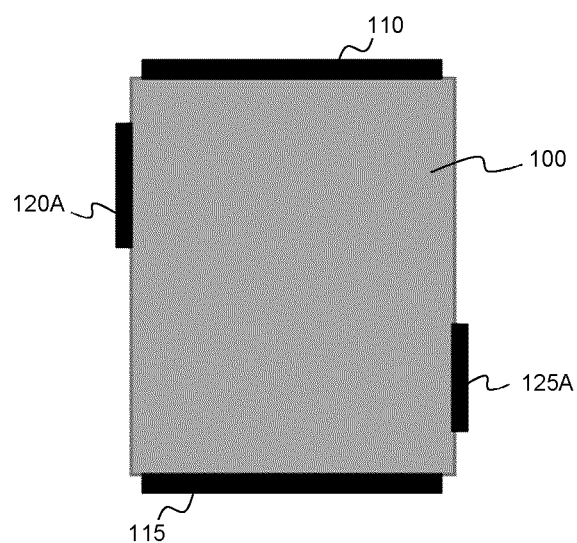

For example, FIGS. 21A and 21B show the acoustic field pattern and spatial cross-section of a biphasic ring ultrasound transducer 250 having propagation electrodes 110, 115, an outer lateral electrode 120 and an inner lateral electrode 125. However, FIGS. 22A and 22B show the acoustic field pattern and spatial cross-section of a biphasic ring ultrasound transducer 250 having propagation electrodes 110, 115, an outer lateral electrode 120A and an inner lateral electrode 125A, where the lateral electrodes 120A and 125A are not spatially aligned in the propagation direction and are smaller in size than in FIG. 21B. In this example, both the biphasic phase difference between the first and second driving waveforms and the relative amplitudes of the first and second driving waveforms were kept constant in both ring transducers. As can be seen by comparing FIG. 21A and FIG. 22A, the shifting and reduction in surface area of the lateral electrodes 120A and 125A results in a significant modification of the acoustic field pattern and a visible reduction in side-lobe energy. The ring transducer with a reduced coverage by the lateral electrodes shows an acoustic field that shorter in the propagation direction. This result shows how the arrangement of the electrodes can have an influence in controlling the ultrasound direction Likewise, FIGS. 23A and 23B show the acoustic field pattern and spatial cross-section of a biphasic prismatic ultrasound transducer 100 having propagation electrodes 110, 115, and lateral electrodes 120 and 125. However, FIGS. 24A and 24B show the acoustic field pattern and spatial cross-section of a biphasic prismatic ultrasound transducer 100 having propagation electrodes 110, 115, and lateral electrodes 120A and 125A that are not spatially aligned in the propagation direction. In this example, both the biphasic phase difference between the first and second driving waveforms and the relative amplitudes of the first and second driving waveforms were kept constant in both prismatic transducers. As can be seen by comparing FIG. 23A and FIG. 24A, the shifting and reduction in surface area of the lateral electrodes 120A and 125A results in a significant modification of the acoustic field pattern, with the asymmetric and misaligned lateral electrode embodiment of FIGS. 24A and 24B resulting in a bi-directional emission pattern. The prismatic transducer with a reduced coverage on the lateral electrodes shows an acoustic field that steers the ultrasound energy in two directions, compared to a single direction with the transducer with electrodes covering a larger surface area. This result shows how the arrangement of the electrodes can have an influence in controlling the ultrasound direction.

Accordingly, in some example embodiments, a biphasic ultrasound transducer may be provided with lateral electrodes that are spatially offset in the propagation direction and the degree of spatial offset and/or the size (or relative sizes) of the lateral electrodes may be selected in order to achieve a desired spatial distribution of the emitted acoustic energy.

In some example embodiments, at least one lateral surface of a biphasic ultrasound device may be provided with an array (plurality) of lateral electrodes (lateral electrode array elements). During operation, one or more of the lateral electrodes array elements of the lateral electrode array may be actuated, thereby providing control over the size and/or location of electrode region that is electrically actuated. The selection of the one or more lateral electrode array elements of the lateral electrode array defined on a given lateral surface may be dynamically selected in order to control a directional property of the emitted ultrasound energy. In some example embodiments, the active electrodes of a given lateral electrode array may be actuated with a common phase, while in other example embodiments, two or more active electrodes of a given lateral electrode array may be actuated with phase difference, and the phase difference may be controlled to further control a directional property of the emitted ultrasound energy.

For example, a given lateral surface may be provided with a set of electrode elements defined in segments. According to various non-limiting example implementations, the electrode array elements may be distributed across the full lateral surface or a portion of the lateral surface, and may be provided in a 1D pattern (e.g. strips), in a 2D pattern (e.g. a grid), or in pseudorandom patterns, with each segment covering a portion of the given lateral face of the biphasic ultrasound transducer.

It will be understood that one or both opposing lateral sides of a biphasic ultrasound transducer may be provided with lateral electrode arrays. For example, in some example implementations, one lateral surface may be provided with an array of lateral electrodes and the other opposing lateral surface may be provided with a single lateral electrode, or alternatively both opposing lateral surfaces may be provided with respective arrays of lateral electrodes.

Accordingly, when a given lateral surface of a biphasic transducer is provided with an array of lateral electrodes as opposed to a single lateral electrode, directional control over the ultrasound energy emitted by a biphasic ultrasound transducer element may be achieved, at least in part, by employing the selective actuation of one or more lateral electrode array elements. The selective actuation of a given lateral electrode array element of a lateral electrode array defined on a given lateral surface of a biphasic ultrasound transducer may be achieved, for example, using one or more electronic switches.

Figure 25A:
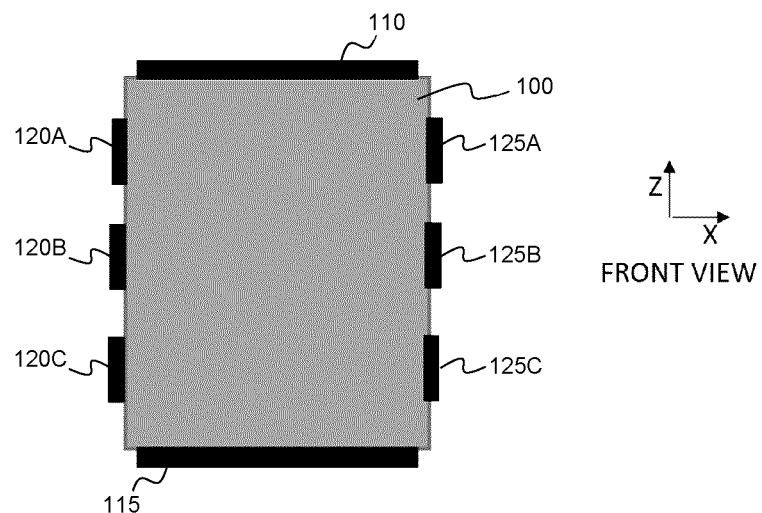
FIGS. 25A and 25B show side views of an example prismatic ultrasound transducer having an array of lateral electrodes, thereby facilitating the selective actuation of one or more of each of the lateral electrodes in order to vary the size and/or location of the lateral electrodes employed to drive the transducer in biphasic mode.
Figure 25B:
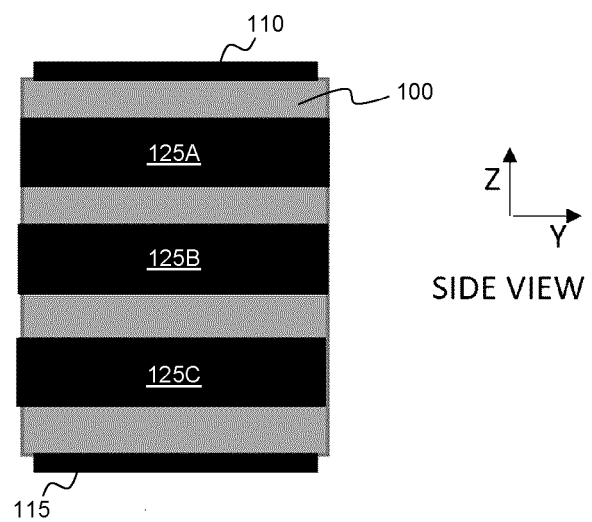

For example, with reference to the example implementation shown in FIGS. 25A and 25B, a biphasic prismatic transducer 100 having propagation electrodes 110 and 115 is shown having lateral electrode arrays (120A-120C and 125A-125D) defined on opposing lateral surfaces. During biphasic operation, the effective size and location of the active lateral electrode region on each lateral surface can be modified by selectively actuation one or more of the lateral electrode array elements.

It will be understood that the present electrode-selection-based directional control method may be employed in alternative to, or in addition to, the previously described directional control methods based on control of one or more of a phase difference between the first driving waveform and the second driving waveform and an amplitude ratio between the first driving waveform and the second driving waveform.

While many of the preceding example embodiments have described systems and methods that employ biphasic driving of individual ultrasound elements to control one or more directional properties of the emitted ultrasound energy, these example embodiments may also be employed for the control of ultrasound transducer elements of an ultrasound array. In one example embodiment, one or more ultrasound array elements of the ultrasound array may include propagation electrodes and lateral electrodes, with the propagation and lateral electrodes being respectively driven with biphasic waveforms, and one or more of the phase difference or the relative amplitudes of the biphasic waveforms may be selected to steer the emitted ultrasound energy toward a desired focal region.

Figure 3:
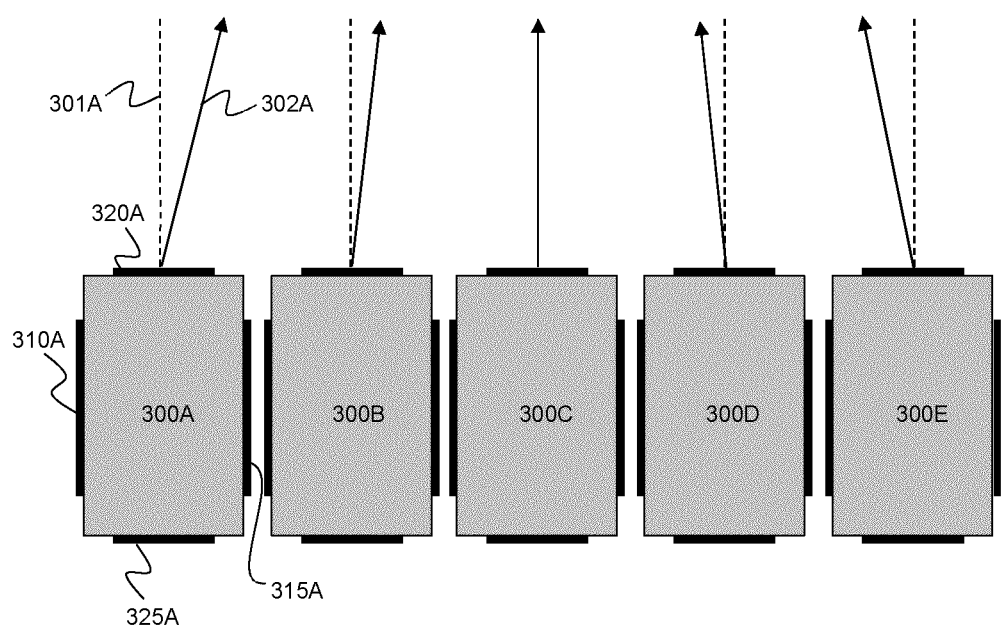
FIG. 3 shows an example linear phased array transducer in which at least one ultrasound transducer element is driven by biphasic driving waveforms to focus the emitted ultrasound energy toward a focal region associated with time-of-flight transmit beamforming.

FIG. 3 illustrates an example one-dimensional ultrasound array that includes array elements 300A-300E. Each array element includes a piezoelectric material and at least two pairs of electrodes. For example, element 300A is shown having a pair of propagation electrodes 320A and 325A that are provided on a first pair of opposing surfaces of the piezoelectric material, such that the propagation electrodes are arranged perpendicular to axis 301A, and a pair of lateral electrodes 310A and 315A are provided on a second pair of opposing surfaces and which are parallel to the axis 301A.

In one example implementation, each array element is driven with biphasic waveforms (delivered to the respective propagation and lateral electrodes) such that the ultrasound energy emitted by each array element is directed at a desired focal region. For example, as shown in FIG. 3, array element 300A is driven with biphasic waveforms such that the ultrasound energy emitted by the array element is directed, as per arrow 302A, at a desired focal region (focus).

Accordingly, in one example embodiment, each ultrasound array element of the ultrasound array may be driven with respective biphasic waveforms such that the ultrasound energy emitted by the set of array elements is focused at a desired focal region. In one example implementation of such an embodiment, biphasic driving and focusing with the ultrasound array may be performed in the absence of time-of-flight beamforming, with the ultrasound energy being focused at the desired focal region based on biphasic focusing alone, provided that the biphasic steering range of each ultrasound array element is capable of directing the emitted ultrasound energy at the focal region. In other example embodiments, biphasic driving may be combined with time-of-flight transmit beamforming. For example, in cases in which the focal region resides beyond a biphasic steering range of at least some of the ultrasound array elements, biphasic driving may be combined with time-of-flight beamforming, such that the combination of biphasic steering toward the focal region, and time-of-flight focusing, achieves the desired focusing.

In some example embodiments, the array elements may be separately formed, e.g. by dicing a piezoelectric material for form individual ferroelectric elements that are subsequently assembled into an array), or may be formed monolithically, e.g. such as via a kerfed array formed in a piezoelectric material.

It will be understood that although many of the present example embodiment pertain to one-dimensional arrays, the embodiments of the present disclosure may be extended to other spatial configurations, such as 1.5 and 2D arrays. Furthermore, while the example ultrasound array shown in FIG. 3 pertains to an array of prismatic ultrasound elements, an ultrasound array may be formed from elements having other geometries. In one example embodiment, an ultrasound array may be formed from a set of concentric transducers have a ring-shaped cross section (e.g. a concentric annular array). In another example embodiment, an ultrasound array may be formed from an array (1D or 2D) of ultrasound transducers having a ring-shaped cross section (e.g. a linear array of annular ultrasound array elements). In such example embodiments, one or more (e.g. all) of the ultrasound transducer elements may be provided with both propagation electrodes and lateral electrodes, and may be driven via biphasic waveforms with directional control via one or both of (i) a phase difference between the biphasic driving waveforms and (ii) a relative amplitude of the biphasic driving waveforms.

Figure 4:
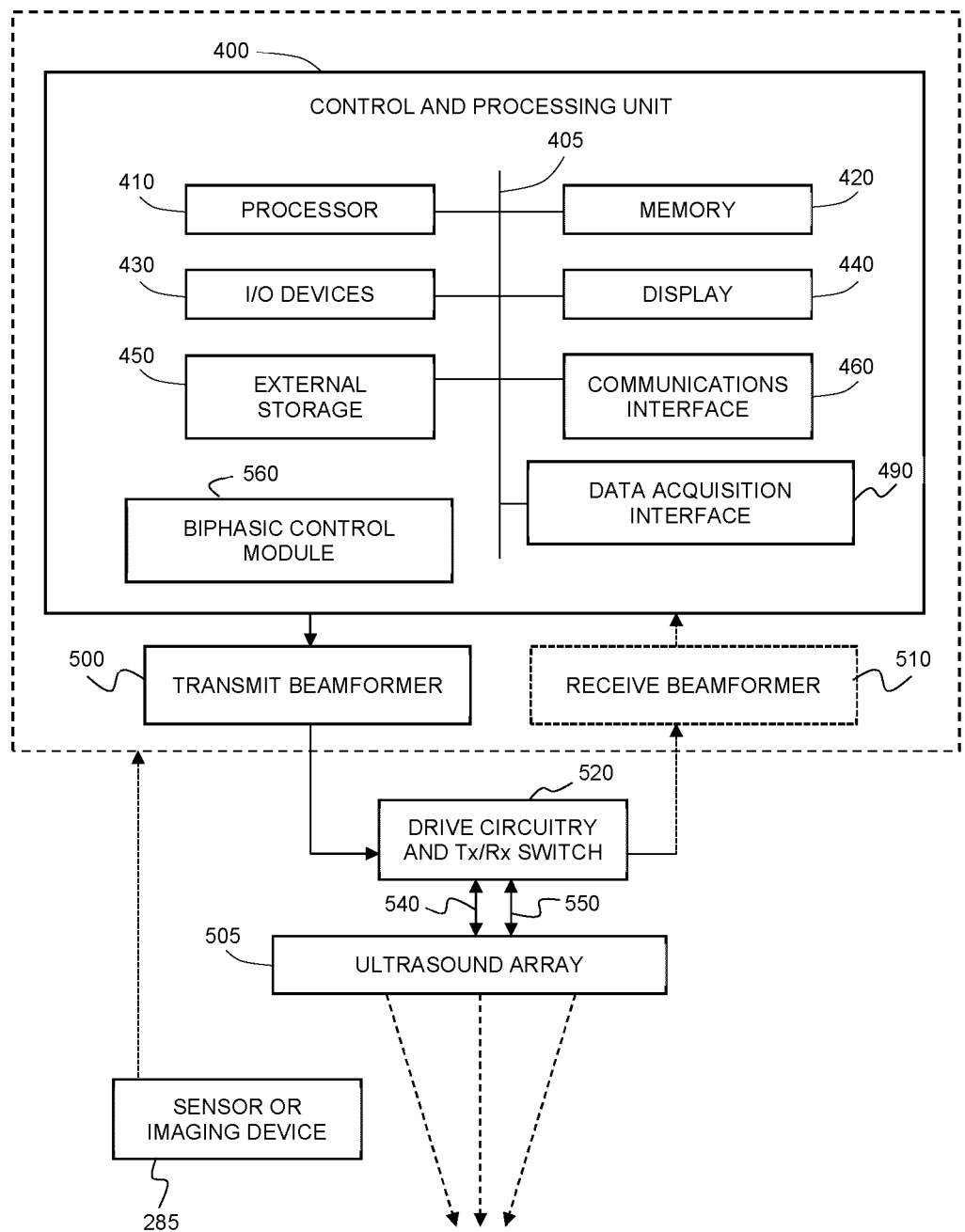
FIG. 4 shows an example system for controlling a phased array ultrasound transducer according to biphasic transmit focusing and optional time-of-flight focusing.

FIG. 4 illustrates an example imaging system for controlling an ultrasound array using biphasic driving and focusing.

The example system includes an ultrasound array 505 having a set of array elements, where at least a subset of the array elements have both propagation and lateral electrodes provided thereon. The electrodes of the ultrasound array 505 are interfaced with drive circuitry 520 (e.g. including voltage sources and amplifiers), which is operably connected to a transmit beamformer 500. For example, for each ultrasound array element having associated propagation electrodes and lateral electrodes, separate propagation electrode connections 540 and lateral electrode connections 550 are provided. The ultrasound array 505 emits ultrasound energy that is focused based on biphasic driving waveforms, of which one or more of a phase differences and a relative amplitude may be controlled according to one or more methods of the present disclosure. For example, the biphasic drive waveforms that are applied to the propagation and lateral electrodes (as a potential difference) with a suitable phase difference (the biphasic drive signals) may be provided on a per-element basis by a transmit beamformer, as shown in FIG. 4. Briefly, a short electric pulse is generated and multiplexed to be sent to individual elements of the phase-array after applying a phase difference and/or relative amplitude scaling. In example implementations involving imaging, the system may include a Tx/Rx switch and a receive beamformer 510.

A control and processing unit (circuitry) 400 is employed to control the transmit beamformer 500 and the optional receive beamformer 510, and to process the beamformed signals. For example, the transmit beamformer 500 may be configured to generate a focused ultrasound beam from the ultrasound array 505 based on driving signals alone, or based on a combination of time-of-flight beamforming and biphasic steering. In one example embodiment, the control and processing unit 400 may include a processor 410, a memory 420, a system bus 405, one or more input/output devices 430, and a plurality of optional additional devices such as communications interface 460, data acquisition interface 490, display 440, and external storage 450. It is to be understood that the example system shown in the figure is not intended to be limited to the components that may be employed in a given implementation. For example, the system may include one or more additional processors.

One or more components of the control and processing unit 400 may be provided as an external component that is interfaced to a processing device. For example, as shown in the figure, the transmit beamformer 500 and the receive beamformer 510 may be included as a component of the control and processing unit 400 (as shown within the dashed line), or may be provided as one or more external devices. The biphasic driving module 560 may be configured or programmed to execute algorithms for performing the methods described herein. For example, biphasic driving module 560 may determine suitable values of a phase difference and/or a relative amplitude of the first and second driving signals in order to focus the ultrasound energy emitted by the ultrasound array elements according to a pre-determined relationship. In some example implementations, the biphasic driving module may employ a signal from a cavitation sensor or an ultrasound imaging transducer 285 (separate or integrated with the ultrasound array 505) as a feedback parameter for controlling the one or more directional properties of the emitted ultrasound energy.

Embodiments of the present disclosure can be implemented via processor 410 and/or memory 420. For example, the functionalities described below can be partially implemented via hardware logic in processor 410 and partially using the instructions stored in memory 420. Some embodiments are implemented using processor 410 without additional instructions stored in memory 420. Some embodiments are implemented using the instructions stored in memory 420 for execution by one or more general purpose microprocessors. Thus, the disclosure is not limited to a specific configuration of hardware and/or software.

While some embodiments can be implemented in fully functioning computers and computer systems, various embodiments are capable of being distributed as a computing product in a variety of forms and are capable of being applied regardless of the particular type of machine or computer readable media used to actually effect the distribution. At least some aspects disclosed can be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache or a remote storage device.

A computer readable storage medium can be used to store software and data which when executed by a data processing system causes the system to perform various methods. The executable software and data may be stored in various places including for example ROM, volatile RAM, nonvolatile memory and/or cache. Portions of this software and/or data may be stored in any one of these storage devices.

The example embodiments described in the present disclosure may be employed in a wide variety of applications, including, but not limited to, therapeutic ultrasound treatment and ultrasound imaging. For example, biphasic driving systems and methods disclosed herein may be employed to provide simple, robust and low-cost single-element ultrasound scanning devices that do not require mechanical steering or multiple transducer elements in order to achieve beam scanning. Furthermore, the present example embodiments involving the adaptation of biphasic driving to ultrasound arrays may facilitate the focusing of ultrasound energy beyond the diffraction limit that is associated with conventional array methods, which may find beneficial use, for example, in medical imaging and therapy applications.

In medical imaging, a potential benefit of the biphasic driving in a phased-array is the capability to improve both axial and lateral resolution as the focal spot becomes with smaller dimensions. This may be particularly advantageous because conventional methods using the time-of-flight beamforming required increasing the frequency or number of transducer elements to improve the degree of focusing. For therapy applications, the capability to reduce the size of focal spot may be particularly advantageous for applications in which there is a physical limit of the maximal frequency or limited by accessibility constrains.

One example of such an application is transcranial therapeutic applications of focused ultrasound, where the maximal frequency is often below 1 MHz because the skull attenuates too much energy, in which case it can be challenging to improve the degree of focusing. The present example biaxial driving methods may be employed to facilitate the use of frequencies compatible with transcranial ultrasound, while also improving the degree of focusing. This may facilitate improving therapeutic ultrasound applications involving the brain, such as thermal therapy with focused ultrasound, drug-delivery with focused ultrasound, neuromodulation with focused ultrasound and more. The capability to produce tighter focal spots may permit the targeting of much smaller structures in the brain, which is particular advantageous for neuromodulation applications that often target regions in the brain in the millimeter- or sub-millimeter scale. Moreover, the present example biphasic steering methods may be useful in therapeutic applications for essential tremor and tremor-dominant Parkinson's disease, where a high degree of accuracy in targeting brain tissue for lesioning is required. Furthermore, the present example methods may be employed for numerous oncology applications in which where tumor ablation is required.

Other applications in which the transducer must located in close proximity to the target region (non-limiting examples of which include endovaginal devices targeting uterine targets, endorectal devices targeting the prostate, endoesophegeal devices targeting esophagus or the heart, intravenous devices targeting cardiac tissue, endogastric devices targeting stomach wall, superficial devices targeting the skin) may benefit from the present biaxial driving methods because tighter focal spots can be produced with fewer transducer elements, which can enable the use of devices with smaller dimensions, which will facilitate more ergonomically-friendly designs.

EXAMPLES

The following examples are presented to enable those skilled in the art to understand and to practice embodiments of the present disclosure. They should not be considered as a limitation on the scope of the disclosure, but merely as being illustrative and representative thereof.

In the following examples, the feasibility of employing biaxial driving of ultrasound transducer elements for directional control is demonstrated. It is shown that a controlled steering can be achieved in single element ultrasound transducers using the biaxial driving technique. Steering angles up to 34° are demonstrated using a single prismatic element and two orthogonal driving signals. Numerical simulation results demonstrate that, when combined with conventional focusing methods, biaxial transducer phased-arrays are expected to facilitate higher focusing compared to traditional time-of-flight methods alone.

Furthermore, in the case of low-power narrowband single element biaxial piezoceramic transducers, the acoustic efficiency is shown to be increased relative to that obtained using conventional driving methods. Excellent agreement is found between finite element simulations and experimental results, with the frequency response differing by a maximum of 6.0% and the efficiency by 13.7%±1.4%, which can be related to a lossless system simulation. It is also demonstrated that the addition of a second set of electrodes does not produce a change in the efficiency response of the ultrasound transducer.

Additional experimental results also demonstrate the control of the location and size of the focal region of a single element ring-type transducer, where the biaxial method can produce focal steering along the acoustic axis direction.

Figure 5:
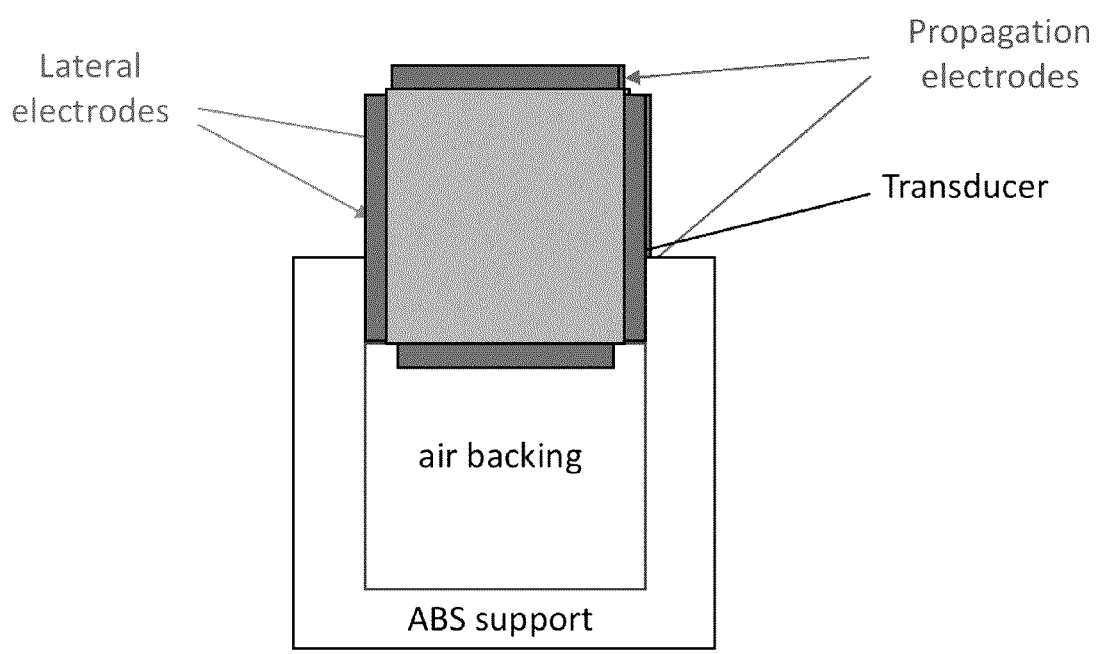
FIG. 5 provides a schematic of a prismatic biaxial single transducer.

Example 1: Prismatic Transducer Element Experiments and Simulations 1.1—Finite Element Analysis (FEA) Simulation Finite-element analysis was employed to numerically characterize the biaxial effect in piezoelectric transducers. The geometry of the simulated prismatic transducer device is shown in FIG. 5. The prismatic transducers were designed with a central frequency of 133 kHz. Finite element analysis (FEA) was employed evaluate the optimal driving conditions for single element biaxial transducers made of a Lead Zirconate Titanate (PZT) piezoceramic material (DL-47, Del Piezo Specialties, LLC, West Palm Beach, FL, USA). Harmonic analysis was performed in a frequency range from 100 kHz to 150 kHz with 1 kHz-resolution. The simulations were performed using the Workbench 19.2 software (ANSYS, Canonsburg, PA, USA).

Figure 6:
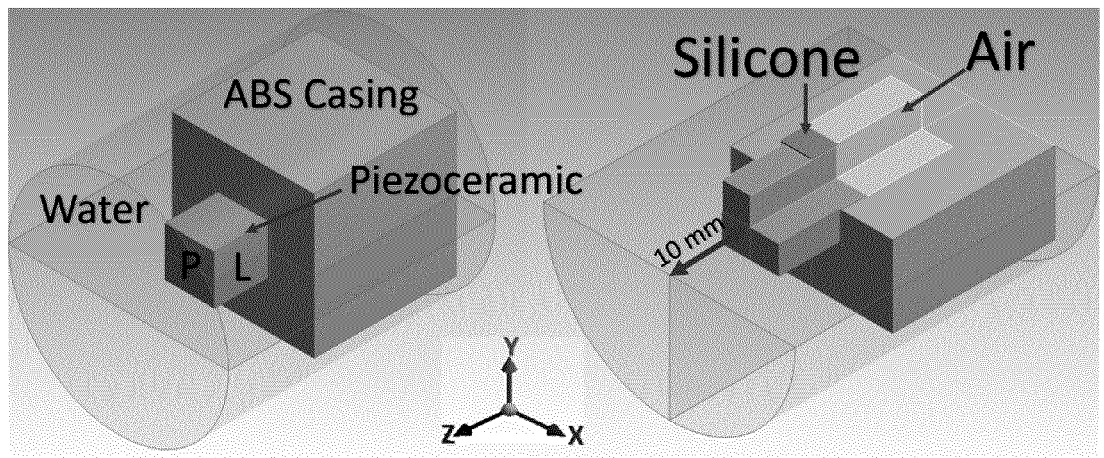
FIG. 6 shows the finite element analysis 3D model of a biaxial transducer poled along the propagation direction (Z-Axis). Conventional excitation of the transducer is performed by applying an electric field to the propagation faces P (Z-Axis). Biaxial excitation is done by applying an additional orthogonal electric field to the lateral faces L (X-Axis).

The simulated piezoceramic had a 7-mm×6.9-mm×10.6-mm (xyz) rectangular shape poled along the propagation (z) axis, and had a 20×20×20-mm ABS plastic cubic enclosure case, with air as the backing material. A 0.6 mm-thick silicone layer was included on the segment of the piezoceramic lateral (x) faces that are in direct contact with the ABS casing. As shown in FIG. 6, a water cylinder with a radius of 15.5 mm and height of 37.5 mm was used in the simulations as the propagation media with a mesh size of 1.5 mm for all the 3D model parts. The propagation (P, front and back faces, perpendicular to z) and lateral (L, right and left faces, perpendicular to x) electrodes were modeled as a coupled equipotential set of nodes. An acoustic absorption boundary condition was employed on the outer walls of the water media to avoid reflected waves.

1.1.1 Conventional Driving Simulation

FEA simulations of a conventional transducer were performed by driving the transducer model with a single electric field applied along the propagation axis. A sinusoidal signal was applied with a voltage that produced an electric power of 2 W at the propagation resonance frequency. This voltage value was kept constant for the range used in the harmonic analysis. The electric impedance, the applied electric power ($W_E$), the acoustic power ($W_A$) on the water cylinder face 10 mm away from the face of the transducer, the acoustic pressure on the XZ-plane, and the acoustic efficiency ($\eta$) were calculated, where:

$$\eta = \frac{W_A}{W_E} \times 100\%. \quad (1)$$

1.1.2 Biaxial Driving Simulation

Two orthogonal electric fields, connected to independent simulated sinusoidal signals, were applied to model biaxial driving conditions. A series of FEA simulations were performed to study the acoustic efficiency and beam profile as a function of the phase $\phi$ between the driving signals and of the power, $p_l$, applied to the lateral electrodes. The power at the propagation electrodes was kept constant for all simulations and set to 1 W at resonance frequency. Values of $\phi$ ranging from 0° to 315° were tested with a 45° step for values of $p_l$ of 0.1 W, 0.5 W and 1 W. FEA harmonic analysis was performed, where the electric impedance at both electrodes, the sum of the effective electric power at both electrodes ($W_E$), the acoustic power ($W_A$) on the water cylinder 10 mm away from the face of the transducer and the acoustic pressure on the XZ-plane were calculated for every $\phi$ and $p_l$ tested. The acoustic efficiency ($\eta$) was calculated as a function of $\phi$ and $p_l$ with $$\eta(\phi, p_l) = \frac{W_A(\phi, p_l)}{W_E(\phi, p_l)} \times 100\%. \quad (2)$$

Figure 7:
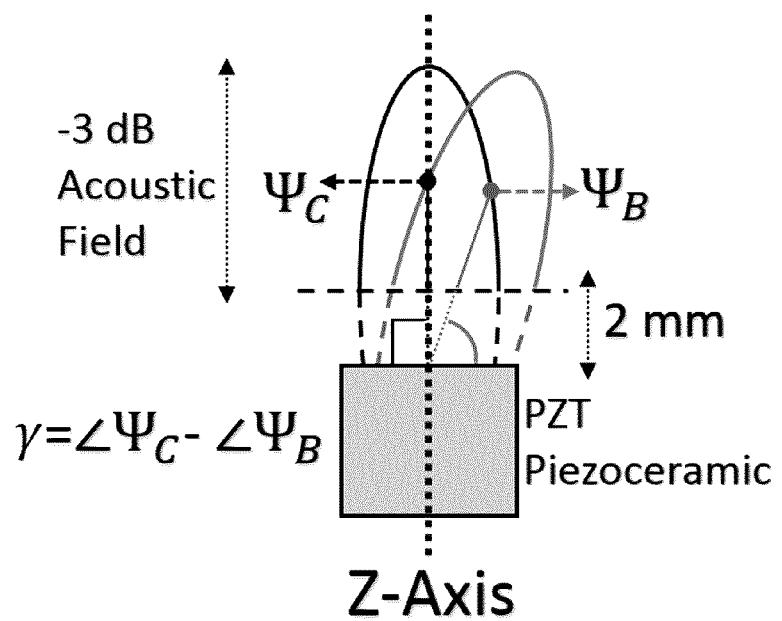
FIG. 7 geometrically illustrates the calculation of $\gamma$ as the angle between the vectors formed by $\Psi_C$ and $\Psi_B$ of the biaxial transducer within the −3 dB normalized acoustic pressure field under different $\phi$ and $p_l$ values. A 2 mm-compensation was applied on the Z-axis to match experimental measurement conditions.

As shown in FIG. 7, the steering angle $\gamma$ of the ultrasound beam produced by the biaxial driving technique was calculated by analyzing the acoustic beam profiles generated by the transducer. First, the centroid ($\Psi$) in the XZ-plane was calculated within the −3 dB region of the normalized acoustic pressure distribution for the conventional ($\Psi_C$) and the biaxial ($\Psi_B$) driving conditions. $\gamma$ was defined as the angle between the vectors formed by $\Psi_C$ and $\Psi_B$, for all the tested combinations of $\phi$ and $p_l$ at the propagation resonance frequency. A 2 mm offset was applied in the calculations of $\Psi_C$ and $\Psi_B$ to match the experimental acoustic pressure measurements.

1.2—Experimental Validation of Efficiency and Steering of Biaxially Driven Transducers 1.2.1 Fabrication Three biaxial transducers were fabricated with the geometric characteristics described above in section 1.1 (identified by $B_i$, where i is the transducer number) and three conventional transducers (identified by $C_i$) using the same piezoceramic type and dimensions. For the conventional transducers, a set of electrodes were provided for excitation along the propagation axis. For the biaxial transducers, two attached sets of electrodes were provided, one set being provided for excitation along propagation axis (the propagation electrodes) and one set of lateral electrodes. A drop of silver epoxy (8331S-15G, MG Chemicals, B.C., Canada) was applied to strengthen the solder joint of each electrode, and the piezoceramic was secured to the sides of a 3D printed ABS casing (Taz 5, Lulzbot, Colorado, USA) using silicone (Silicone I*, Momentive Performance Materials Inc., NC, USA) with air as backing material.

Figure 8:
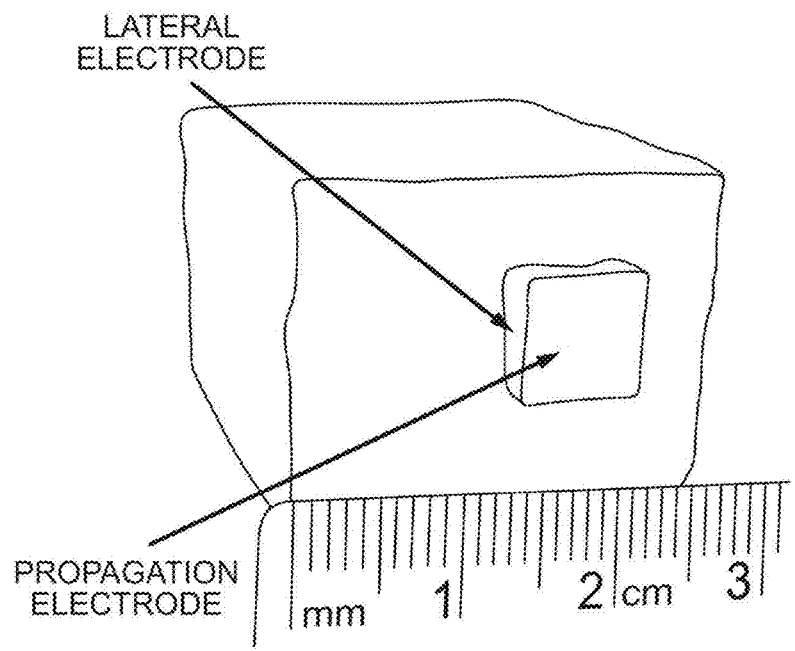
FIG. 8 is a photograph of a single-element biaxial transducer.

A vector network analyzer (ZNL3, Rode & Schwarz, Munich, Germany) was employed to determine the resonance frequency for each transducer as the frequency at which the lowest value of impedance was measured. Impedance for all transducers was matched to 50Ω at resonance frequency. For biaxial transducers, the propagation and the lateral modes were matched separately. FIG. 8 shows an example of one of the custom-built biaxial transducers.

Figure 9:
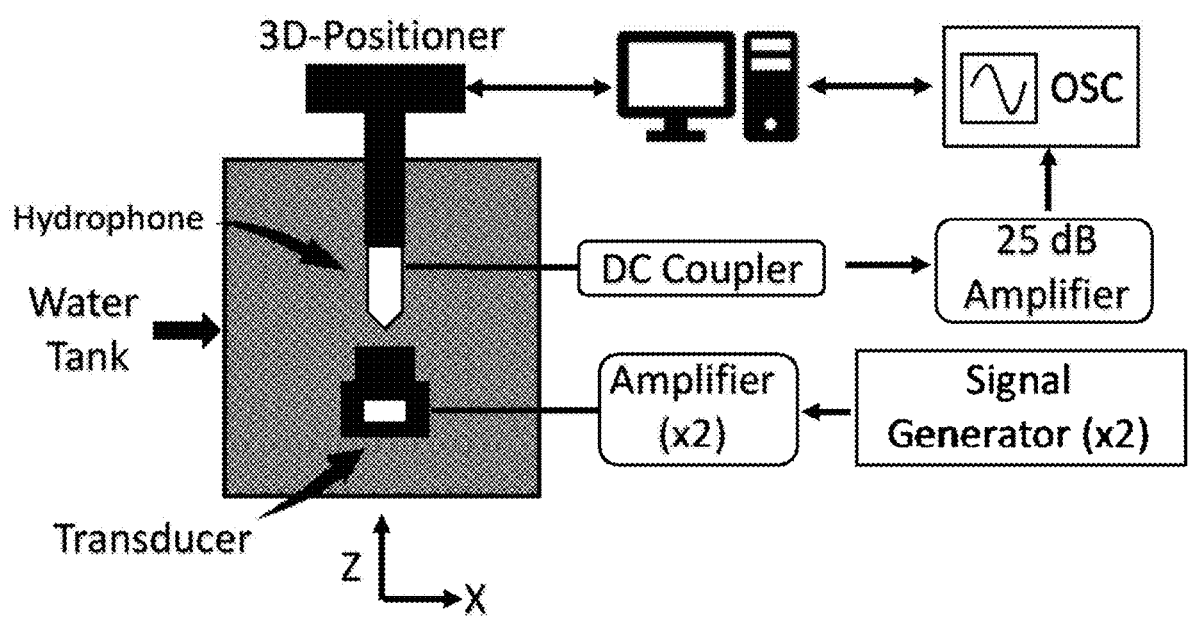
FIG. 9 is a schematic illustration of the apparatus employed to perform acoustic characterization of the fabricated transducers.

Acoustic pressure characterization (FIG. 9) of each transducer was performed using a 2 mm-diameter needle hydrophone (NH2000, Precision Acoustics, Dorset, UK). The hydrophone was mounted on a robotic 3D-positioner system (UMS3 Scanning tank, Precision Acoustics, Dorset, UK) placed 2 mm away from the transducer inside a tank filled with deionized and degassed water. The conventional transducers were driven with a 2-cycle-sinusoidal burst, at a burst repetition frequency of 100 Hz produced by a dual-channel function generator (33522A, Agilent Technologies, Santa Clara, CA), and amplified (240L, E&I, Rochester, NY) to reach a power of 1 W at the resonance frequency of the transducer.

The biaxial transducers were driven with a 2-cycle sinusoidal burst using the propagation resonance frequency, at a burst repetition frequency of 100 Hz and a power of 1 W on the propagation electrodes. The same range of values of $\phi$ and $p_l$ as in the FEA were tested: $\phi$ ranged from 0° to 315° with a 45° step and $p_l$ was 0.1 W, 0.5 W and 1 W. For the hydrophone measurements of the biaxial transducers, the order of combinations of $\phi$ and $p_l$ were randomized. The acoustic field was measured with the hydrophone on the XZ-plane using a 0.5-mm resolution step. The region covered on the X-axis ranged from −4 mm to +4 mm from the center of the transducer, while on the Z-axis ranged from 2 mm to 8 mm away from the transducer. The hydrophone measurements were coupled (DC Couple with Power Supply, Precision Acoustics, Dorset, UK), amplified (Hydrophone Booster Amplifier, Precision Acoustics, Dorset, UK) and digitized with an oscilloscope (DSOX3024A, Keysight, Santa Rosa, CA). To provide a baseline of the beam profile for the calculation of the steering angle $\gamma$, acoustic pressure characterizations were performed with the biaxial transducers using only the propagation electrodes with 1 W power.

For each of the biaxial transducers, γ was calculated as the angle between the vectors formed by the centroid of the biaxial transducer with conventional driving $\Psi_C$ and $\Psi_B$ (similar as described above in Subsection 1.1.2) using a −3 dB threshold as shown in FIG. 7. The measured acoustic pressure fields were normalized and interpolated to a 0.1 mm resolution.

1.2.2 Acoustic Efficiency Characterization

To characterize the acoustic efficiency of the conventional transducers, a continuous sinusoidal wave was produced by a dual-channel function generator (33522A, Agilent Technologies, Santa Clara, CA) and amplified (240L, E&I, Rochester, NY). The sinusoidal signal had a power of 2 W at the transducer resonance frequency as measured by a power meter (N1914A, Agilent Technologies, Santa Clara, CA). The acoustic power was measured using an analytical scale (NewClassic MS, Mettler Toledo, Columbus, USA) using the radiation force method. The transducer was positioned pointing downward, and 2 cm away from a 6 cm-diameter absorber (HAM A, Precision Acoustics, Dorchester, Dorset, UK) placed on the bottom of a reservoir filled with deionized and degassed water. The acoustic power was calculated as follows:

$$W_A = \frac{mgc}{\cos \gamma'} \quad (3)$$

where m is the change of mass measured by the analytical scale eight seconds after continuous driving, g is the gravity constant (9.81 ms$^{-2}$), c the speed of sound in water at room temperature and γ is the steering angle calculated previously. The coefficient $(\cos \gamma)^{-1}$ determines the vertical contribution of the steered acoustic field to the force measured by the analytical scale. The measurements were performed three times on different days.

For the acoustic efficiency characterization of the biaxial transducers, two independent sinusoidal signals were applied to each set of electrodes and different ϕ and $p_l$ values were employed when delivering signals to the lateral electrodes while keeping 1 W at the propagation electrodes. Each biaxial transducer was driven with a dual-channel function generator (33522A, Agilent Technologies, Santa Clara, CA) and two power amplifiers (240L, E&I, Rochester, NY and AG 1021; T&C Power Conversion, Rochester, NY). The frequency of the driving signals for both pairs of electrodes was set to the propagation resonance frequency. The effective power delivered to each set of electrodes was measured using two power meters (N1914A & E4419B, Agilent Technologies, Santa Clara, CA). The values ranged from 0° to 350° with a 10° step for each value of $p_l$ (0.1 W, 0.5 W and 1.0). Three repetitions were performed per transducer and combination of ϕ and $p_l$. The order of the combinations of ϕ and $p_l$ were randomized within each repetition, and repetitions were performed on different days. $W_A$ and η were obtained using Equations (3) and (2), respectively. Measurements of $W_A$ were also performed while driving the biaxial transducers with only the propagation electrodes with a sinusoidal signal of 2 W to produce a baseline for the comparison of the efficiency produced by the biaxial transducers driven in conventional mode.

1.3—Results 1.3.1 Electrical Impedance Response

Figure 10:
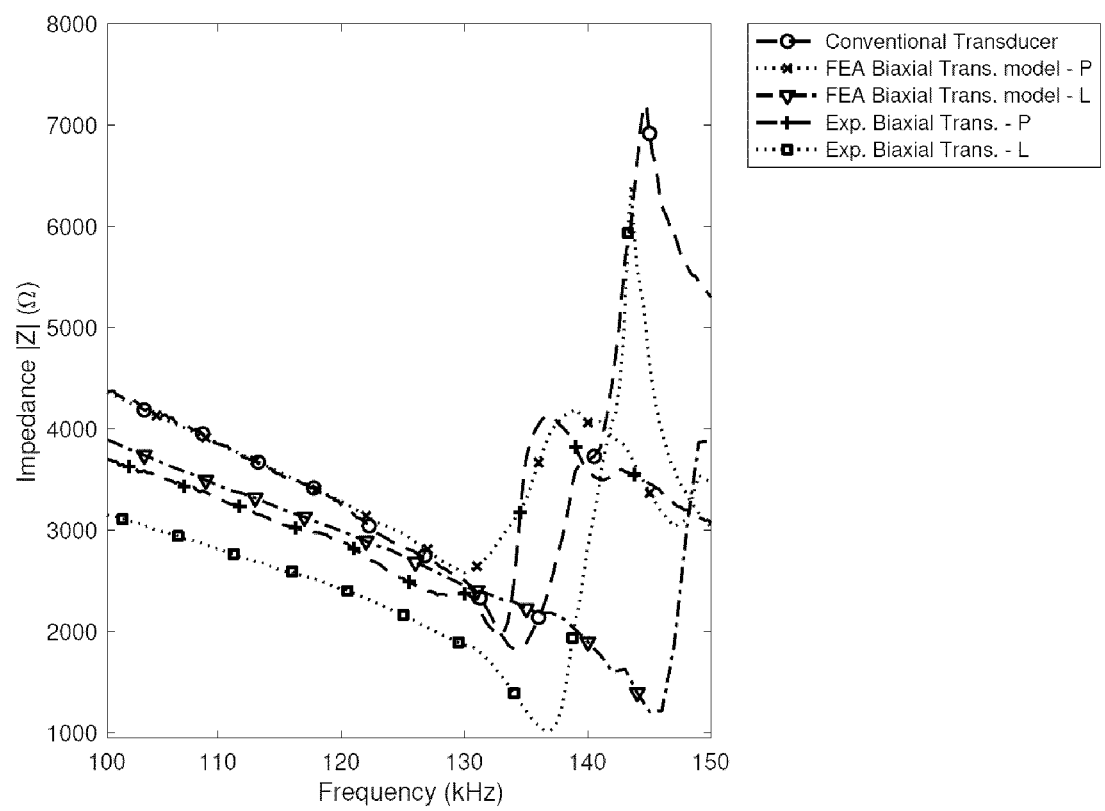
FIG. 10 plots a comparison of the average impedance at the propagation (P) and lateral (L) electrodes between the FEA transducer model and the experimental (Exp) biaxial and conventional transducers.

The FEA model predicted a resonance frequency and impedance of 130 kHz and 2582Ω, respectively, at the propagation electrodes. For the lateral electrodes, the FEA model predicted values of 145 kHz and 1210Ω, respectively. The mean (±s.d.) measured resonance frequency of the three biaxial single-element transducers was 132.75±0.25 kHz on the propagation electrodes with an impedance of 1965.70±62.10Ω. For the lateral electrodes, the average resonance frequency and impedance were 136.80±0.52 kHz and 991.30±102.30Ω. For the three conventional transducers, the average resonance frequency was 134.25±0.66 kHz with an average impedance of 1791.30±168.60Ω. FIG. 10 shows a comparison between the simulated and experimental impedance measurements.

The impedance response observed in simulations and experiments for the biaxial transducer showed an excellent agreement. The resonance frequencies for the propagation and lateral modes showed an absolute difference of only 2.8 kHz and 8.2 kHz, respectively, which corresponded to a relative difference of 2.1% and 6.0%. Experimentally, the conventional transducers and the biaxial transducers showed a difference in their propagation resonance frequency of only 1.5 kHz, corresponding to a relative difference of 1.1%. The relative difference in the on-resonance impedance was 8.8%. The absolute average impedance difference between experiments and simulation for the propagation electrodes was 616.3Ω, and 218.7Ω for the lateral electrodes, which corresponded to a relative difference of 24% and 18%, respectively. Without intending to be limited by theory, the difference in the impedance values was attributed to a clamping effect produced by the silicone used to glue the piezoceramic to the ABS casing.

1.3.2 Acoustic Pressure Field Comparison: Steering Angle

Figure 11A:
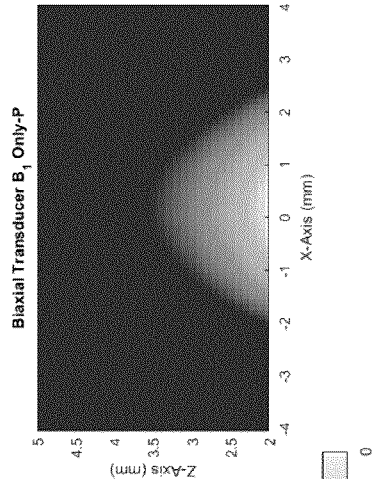
FIGS. 11A-11C plot normalized acoustic pressure field (dB), showing acoustic pressure measured (A) on the conventional transducer C_1, (C) on the propagation-only mode for the biaxial transducer B1, and (B) calculated from FEA transducer model.
Figure 11B:
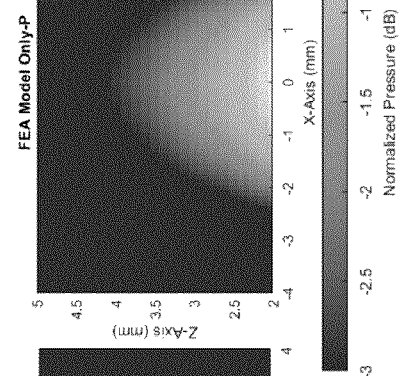
Figure 11C:
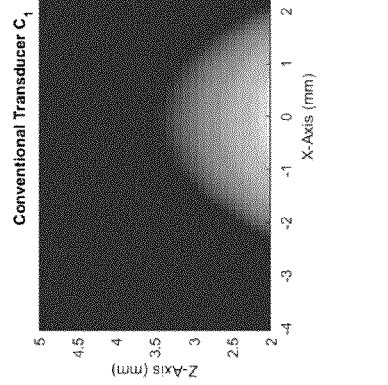

FIGS. 11A-11C and 12A-12D show the normalized acoustic pressure field of the XZ-plane in a logarithmic scale obtained from the FEA biaxial transducer model, the experimental biaxial transducer, $B_1$, and the conventional transducer, $C_1$. When using conventional driving, as shown in FIGS. 11A-11C, the FEA model predicted an ultrasound beam directed with a 0°-angle relative to the Z-axis, which is expected in ideal conditions. The largest steering angles, γ, were predicted by the FEA model for lateral power $p_l$=1 W (as shown in FIGS. 12A and 12B), showing a maximum steering of γ=40.8° for a phase in the lateral electrode of ϕ=315°, and γ=−25.3° for ϕ=90°. FIGS. 12C and 12D show the experimental acoustic profiles of the biaxial transducer $B_1$ for the corresponding values of ϕ and $p_l$ where steering angles of 31° and −32.8° were obtained, respectively. The FEA and experimental acoustic profiles presented an asymmetric response between the achieved steering in the positive (right) and negative (left) direction.

FIGS. 13A-13C plot finite-element (ANSYS 19.2) simulations of the acoustic field (dB scale) in biaxial prismatic transducer operating at 133 kHz where steering (α) of ultrasound appears modified in function of the de-phase angle (ϕ), showing the acoustic field on a larger logarithmic scale. A power of 1 W was applied for the propagation electrodes and 1 W for the lateral electrodes (energy ratio, $E_R$=1). Three different cases were simulated, as shown: (A) without biaxial driving (only-P), which is standard driving method where the beam is generated "straight" up in the sound propagation (Z); (B) with biaxial driving having a dephase angle of 90° (FEA Model ϕ=90°) showing steering towards the left of the transducer); and (C) with biaxial driving having a dephase angle of 315° (FEA Model ϕ=315°) showing steering towards the right of the transducer.

FIG. 14 shows the FEA and experimental results of the steering angle γ as a function of the phase ϕ for all tested values of applied lateral power $p_l$. The FEA model predicted a sinusoidal-type response between γ and ϕ, and the experimental results showed an excellent agreement with this prediction. The maximal steering increased as a function of the applied lateral power $p_l$. The highest average steering γ for the measured biaxial transducers was 32.4°±1° for a ϕ=270° and −36.3°±2.7° at ϕ=180ϕ°, for a $p_l$=1 W. FIG. 15 provides a table showing a summary of the findings.

1.3.3 Efficiency vs. Phase and Power

The FEA biaxial transducer model showed a maximum efficiency, η, of 48% at 126 kHz for the biaxial driving with ϕ=45° and $p_l$=0.1 W. When using conventional driving, η had a value of 47.7% showing that the biaxial driving can outperform the conventional driving even under ideal conditions. Experimental results for the three conventional transducers showed an average η of 31.2% (±2.3%) when driven at their resonance frequency. When the three biaxial transducers were driven through only the propagation electrodes, the average η was 30.3% (±3.9%) at their propagation resonance frequency. The biaxial transducers $B_1$, $B_2$, and $B_3$ produced maximum efficiency of 34.3% (±1.4%), 34.3% (±2.0%) and 28.7% (±1.6%), respectively, for corresponding values of of 310°, 30° and 350°. All the biaxial transducers showed this maximal efficiency with $p_l$=0.1 W. The average maximal efficiency of the biaxial transducers was 32.4% (±3.2%), which was higher than conventional transducers, matching the predictions of the FEA model. FIGS. 16A-16E shows η as a function of both predicted by the FEA model and measured for all the different power values tested on the lateral electrodes.

The maximum efficiency predicted by the FEA model was 48.0% with ϕ=45° and $p_l$=0.1 W, while the maximum experimental efficiency with the biaxial transducer $B_1$ was 34.3±1.4% with ϕ=310° and $p_l$=0.1 W. This efficiency difference can be attributed to the fact that the FEA model operated as a lossless system where no damping mechanisms were considered. The maximum efficiency reached in the FEA simulation was found at 4 kHz below the propagation resonance frequency. This result indicates that a potential optimization of the driving conditions could be explored, where it would be feasible to experimentally test several frequencies in addition to the propagation resonance, since it was previously reported that higher efficiencies were reached at frequencies slightly off the propagation resonance. The difference of efficiency between the conventional and biaxial transducers with only the propagation driving was only 0.9%. This observation indicated that the addition of a second set of electrodes on the lateral faces of a piezoceramic does not affect the efficiency.

It is noted that both FEA and experiments indicated that the maximum steering values were found with $p_l$=1 W, while the maximum efficiency was found with $p_l$=0.1 W. These results suggest that there is a trade-off between the efficiency and steering angle.

1.4 Further Analysis

The simulation and experimental results demonstrated that biaxial driving of a single-element transducer can effectively steer the ultrasound beam with the direction controlled using the phase and power applied to the lateral electrodes. To the best of the knowledge of the present inventors, this is the first time that non-mechanical steering of ultrasound using a single element transducer has been demonstrated. As shown in FIG. 14, the steering angle of the beam had a sinusoidal response as a function of ϕ, with the maximum steering angle for the simulation and experimental measurements obtained for a ϕ of 135°±45° and 292.5°±31.8°, for a left and right steering, respectively. Decreasing the power from 1 W to 0.1 W on the lateral electrode while keeping 1 W on the propagation electrode reduced the maximum steering value that could be obtained, meaning that we can control steering by either reducing the power on the lateral electrodes or by changing the difference in phase between electrodes. The absolute difference in maximum steered angle between the FEA model and the averaged biaxial transducers was 9.7° and 6° for ϕ values of 315° and 90° respectively, both at a $p_l$ of 1 W.

Other than the steering capabilities, the addition of the second set of electrodes did not produce significative variations in the acoustic field. This observation suggests that a supplemental third set of electrodes could be implemented on this rectangular structure to produce a steered beam on the YZ-plane in addition to the reported XZ-plane steered beam.

Figure 17A:
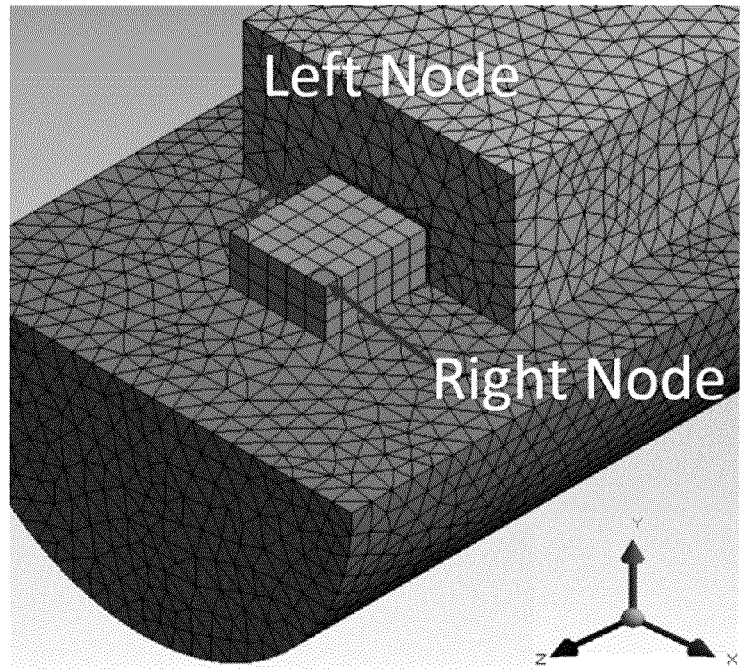
FIGS. 17A and 17B show (A) the location of the right and left node on the front face of the piezoceramic within the FEA model, and (B) the deformation (Z-axis) vs frequency response of the right and left nodes. The lateral and propagation resonance frequency are 145 kHz and 130 kHz respectively for the FEA biaxial model.
Figure 17B:
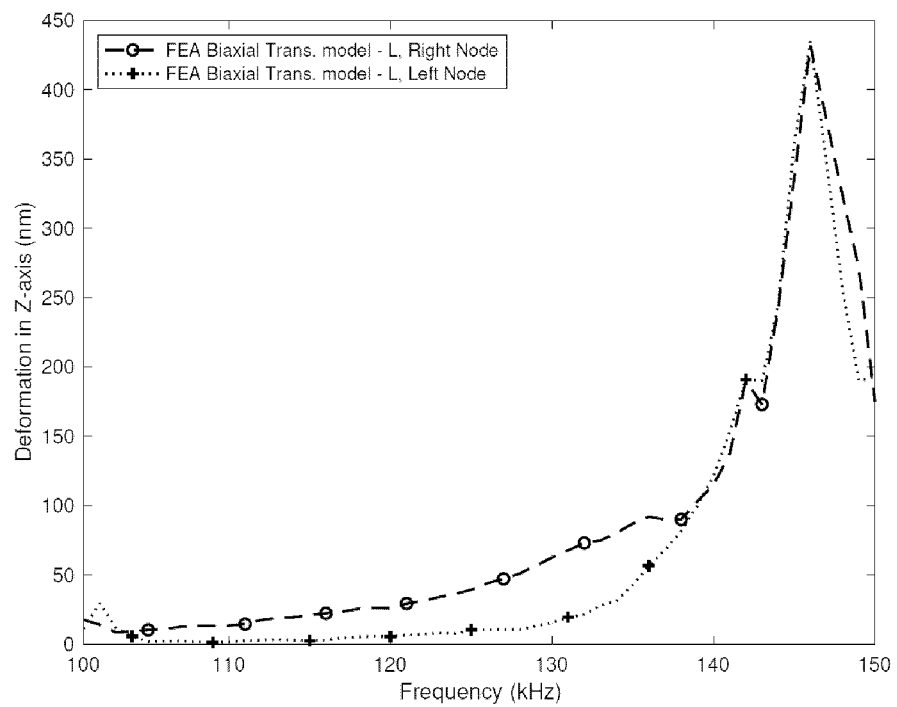

It is noted that nonsymmetric response for the steering γ observed in the simulated and experimental acoustic profile of the biaxial transducers may be related to the driving frequency employed for the lateral electrodes and the amplitude of the deformation produced on the piezoceramic with respect to the Z-axis. The amplitude of the deformation with respect to the Z-axis of two opposite corner nodes (right and left) on the front face of the FEA model was calculated for the range used in the harmonic analysis while driving only the lateral electrodes. The two nodes within the FEA model are shown in FIG. 17A. It was found that for the simulated resonance frequency of the lateral electrodes (145 kHz), the right and left nodes had a deformation of 336 nm and 361 nm, respectively, showing a difference of 25 nm. However, because the lateral electrodes were driven at the propagation resonance frequency (130 kHz on the FEA model) during the biaxial excitation, the amplitude of the deformation for the right and left nodes at that frequency changed to 62.4 nm and 15.5 nm respectively showing a difference of 46.9 nm between nodes. This 87.6% deformation difference between nodes explains the asymmetric steering response because the piezoceramic deformation produced by the lateral excitation losses symmetry as we move away from its resonance frequency. This also explains the higher steering response asymmetry observed in the FEA model compared to the experimental measurements, since the difference between the propagation and lateral resonance frequency in the simulation was 15 kHz while the experimental difference was only 4.1 kHz. FIG. 17B shows the deformation vs frequency response of the right and left nodes.

1.5 Simulation of Phased Array with Biphasic Focusing of Array Elements

The ability to control the directional properties of ultrasound energy emitted by a single transducer element may be significant potential for improving the focusing of ultrasound in phased arrays. A biphasic phased-array example was illustrated by adapting the aforementioned FEA (ANSYS) model for use with PZFlex FEA software (OnScale, Redwood City, CA, USA), which is better suited for phased-arrays. FIGS. 18A-18E present a numerical proof-of-concept demonstrating how the biaxial method can improve focusing dramatically with a 3-element phased-array design. The individual transducer elements employed in the model are identical to the those described above in the single-element FEA studies and experiments. The transducer elements were driven at a frequency of 133 kHz.

Various conditions were simulated in order to demonstrate the improvement of focusing with the biaxial method when compared to traditional time-of-flight (TOF) focusing methods, which is standard in the operation of phased arrays. In the simulations, the TOF method was applied to focus the ultrasound beam 32 mm away from the center of the array in the propagation direction. For the biaxial tests, steering was applied on the left and right elements to converge the ultrasound beam at the desired location. Both the biaxial alone and the biaxial+TOF steering produced a much smaller focal region, with only the biaxial+TOF achieving focusing centered at the intended location of 32 mm, while the traditional+TOF was centered at 54 mm. Moreover, the focal region (area at −6 dB) was reduced from 1514 mm² for the traditional+TOF method, to 810 mm² when using the biaxial+TOF method. These results suggest that even for a simplistic 3-element phased-array, a significant change can be realized using controlled biphasic driving of ultrasound transducer array elements, suggesting that the biaxial method may be capable of overcoming the diffraction limit that is encountered in traditional phased arrays.

1.6 Simulation of Prismatic Transducer with Different Patterns of Lateral Electrodes The ability to control the directional properties of ultrasound energy emitted by modifying the patterns of the electrodes on a prismatic transducer has significant potential for controlling the focusing of ultrasound. A biphasic prismatic transducer was illustrated by a FEA (COMSOL) model. FIGS. 23A and 24A presents a numerical proof-of-concept demonstrating how the steering produced by the biaxial method can be modified by changing the electrodes pattern. The figure shows a comparison between a prismatic transducer that has large coverage in the face where the lateral electrodes are placed and a prismatic transducer that has electrodes that cover a smaller portion of the face. Each transducer has a width of 3 mm, and height of 6 mm. Both left and right sides of the transducers have a 1 mm-width air layer, and another 1 mm-thick air layer is used as backing material. For both prismatic transducers, both the biphasic phase difference between the first and second driving waveforms and the relative amplitudes of the first and second driving waveforms were equal. The transducers were driven at a frequency of 470 kHz and placed inside a 30 mm×40 mm water region.

Various conditions were simulated in order to demonstrate the influence of the surface area covered by the lateral electrodes in the steering capabilities of the transducer. FIGS. 23A and 24A shows the test with a phase difference between lateral and propagation electrodes of 135 degrees, with a voltage of 100 V applied on the propagation electrodes and 70 V on the lateral electrodes. The arrangement on the electrodes with smaller coverage produce a modified steering of ultrasound energy as shown on top of FIG. 24A.

The prismatic transducer with a reduced coverage on the lateral electrodes shows an acoustic field that steers the ultrasound energy in two directions, compared to a single direction with the transducer with electrodes covering a larger surface area. This result shows how the arrangement of the electrodes can have an influence in controlling the ultrasound direction.

Example 2: Ring Geometry 2.1 Fabrication

Figure 19A:
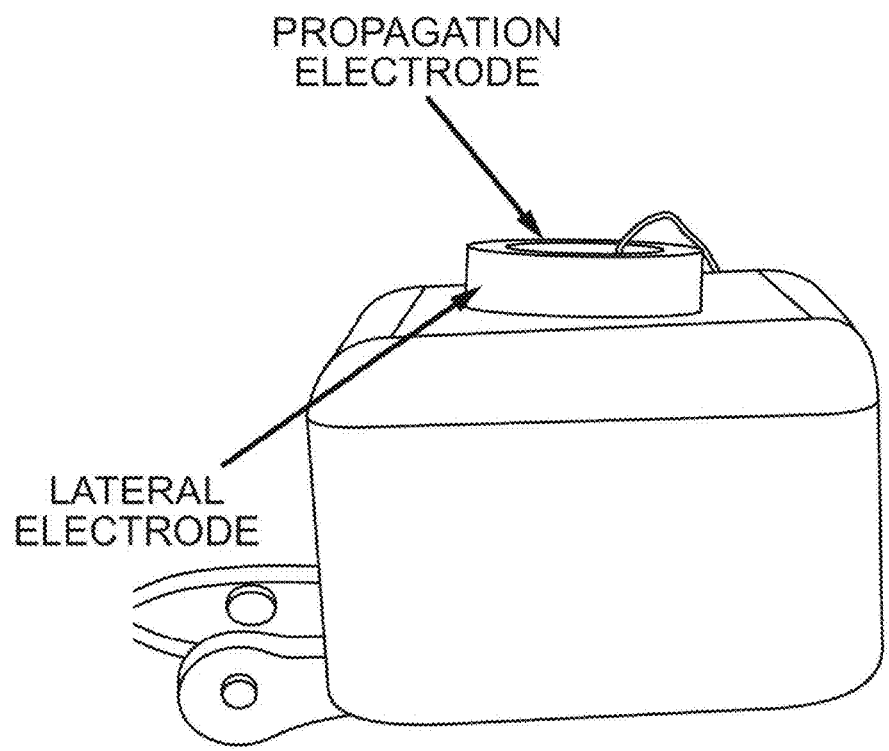
FIG. 19A is a photograph of a prototype ring biaxial transducer.
Figure 19B:
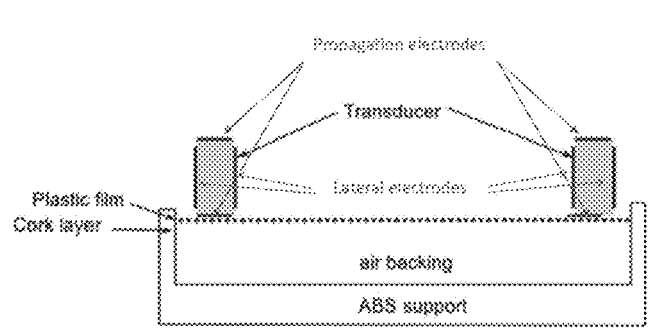
FIGS. 19B and 19C schematically illustrate an example ring biaxial transducer.
Figure 19C:
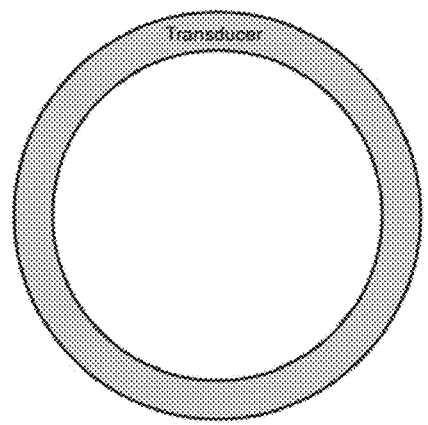

Three ring-shaped biaxial transducers (TR1, TR2, TR3) were fabricated using hard lead zirconate titanate (PZT) (DL47, DeL Piezo Specialities, LLC, West Palm Beach, FL, USA) with an outer diameter of the transducer of 12 mm, a ring width of 3 mm and a height of 6 mm, as shown in FIG. 19A. In addition, the natural resonance frequency of the transducers was specified to be as close as possible to 500 kHz. The transducers were configured as air-backed, using a cork layer below the bottom face of the ring, as shown in FIGS. 19B and 19C. An 0.05 mm-thick plastic film was employed to isolate the cork from the transducer. The ensemble was secured on a 3D-printed ABS support (Taz 5, Lulzbot, CO, USA) using epoxy glue (301, epoxy technology, Billerica, MA).

The impedance characterization for each mode was performed using a vector network analyzer (ZNL3, Rohde & Schwarz, Kanata, Ontario, Canada). The average central resonant frequency for TR1, TR2 and TR3 was, respectively, 505 kHz, 497.5 kHz and 502 kHz. Both propagation and lateral electrodes were matched to 50Ω at their respective resonant frequency using a transformer matching. FIG. 19A shows a photograph of an assembled prototype.

2.2 Results

FIGS. 20A and 20B show the experimentally measured acoustic beam profiles for each of the combinations of de-phase $\phi$ and the energy ratio $E_R$ for transducer TR1. Experimental beam profiles demonstrated control over the size and location (Y direction) of the focal region. As ring transducers produce a natural focal location, FIG. 20C is included to show the beam profiles obtained when using only the lateral and propagation electrodes to drive the transducer.

2.3 Simulation of Ring Transducer with Different Patterns of Lateral Electrodes

The ability to control the directional properties of ultrasound energy emitted by modifying the patterns of the electrodes on a ring transducer has significant potential for controlling the focusing of ultrasound. A biphasic ring transducer was illustrated by a FEA (COMSOL) model. FIGS. 21A and 22A present a numerical proof-of-concept demonstrating how the steering produced by the biaxial method can be modified by changing the electrodes pattern. The figure shows a comparison between a ring transducer that has large coverage in the face where the lateral electrodes are placed and a ring transducer that has electrodes that cover a smaller portion of the face. Each transducer has a width of 3 mm, and height of 6 mm and an inner radius of 9 mm. Inner and outer faces of the ring transducers have a 1 mm-width air layer, and another 1 mm-thick air layer is used as backing material. For both ring transducers, both the biphasic phase difference between the first and second driving waveforms and the relative amplitudes of the first and second driving waveforms were equal. The transducers were driven at a frequency of 470 kHz and placed inside a 30 mm×40 mm water region.

Various conditions were simulated in order to demonstrate the influence of the surface area covered by the lateral electrodes in the steering capabilities of a ring transducer. FIGS. 21A and 22A shows the test with a phase difference between lateral and propagation electrodes of 135 degrees, with a voltage of 100 V applied on the propagation electrodes and 70 V on the lateral electrodes. The arrangement on the electrodes with smaller coverage produces a modified steering of ultrasound energy as shown on top of FIG. 22A. The ring transducer with a reduced coverage by the lateral electrodes shows an acoustic field that is shorter in the propagation direction; 13 mm with the partial coverage electrodes vs. 25 mm with the larger coverage electrodes.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A method of directionally controlling an ultrasound transducer element, the ultrasound transducer element comprising a piezoelectric material and further comprising a pair of propagation electrodes respectively contacting first opposing surfaces that are perpendicular to a first direction and a pair of lateral electrodes respectively contacting second opposing surfaces that are perpendicular to the first opposing surfaces, the method comprising:
   actuating the ultrasound transducer element according to a first driving waveform and a second driving waveform, the first driving waveform and the second driving waveform having a common frequency, such that the first driving waveform is applied to the propagation electrodes and the second driving waveform is applied to the lateral electrodes; and
   employing at least one of (i) a phase difference between the first driving waveform and the second driving waveform and (ii) an amplitude ratio between the first driving waveform and the second driving waveform, to control a directional property of ultrasound energy emitted by the ultrasound transducer element.

2. The method according to claim 1 wherein the first driving waveform and the second driving waveform are controlled according to a predetermined relationship between the directional property of the ultrasound energy emitted by the ultrasound transducer element and one or both of (i) the phase difference between the first driving waveform and the second driving waveform and (ii) the amplitude ratio between the first driving waveform and the second driving waveform.

3. The method according to claim 2 wherein the predetermined relationship is determined, at least in part, according to ultrasound measurements.

4. The method according to claim 2 wherein the predetermined relationship is determined, at least in part, according to simulations.

5. The method according to claim 1 wherein the second opposing surfaces are a first lateral surface and a second lateral surface, and wherein at least one of the first lateral surface and the second lateral surface has at least one additional lateral electrode provided thereon; and
   wherein at least one lateral electrode on the first lateral surface and at least one lateral electrode on the second lateral surface are employed to apply the second driving waveform as a potential difference between the first lateral surface and the second lateral surface; and
   wherein the directional property is controlled, at least in part, by dynamically selecting the lateral electrodes that are employed to apply the potential difference.

6. The method according to claim 1 wherein the lateral electrodes comprise a first lateral electrode and a second lateral electrode, and wherein the first lateral electrode and the second lateral electrode have different respective areas.

7. The method according to claim 1 wherein the lateral electrodes comprise a first lateral electrode and a second lateral electrode, and wherein the first lateral electrode is spatially offset in the first direction relative to the second lateral electrode.

8. The method according to claim 1 wherein the directional property is a steering angle.

9. The method according to claim 1 wherein the directional property is a lateral spatial offset of a near-field region of the ultrasound energy.

10. The method according to claim 1 wherein the second opposing surfaces are perpendicular to a second direction, and wherein the ultrasound transducer element is further actuated according to a third driving waveform that is applied to the ultrasound transducer element along a third direction that is perpendicular to the first direction and the second direction; and
    wherein at least one of (i) a phase difference between the first driving waveform and the third driving waveform and (ii) an amplitude ratio between the first driving waveform and the third driving waveform is employed to control the directional property of ultrasound energy emitted by the ultrasound transducer element.

11. The method according to claim 1 wherein the ultrasound transducer element has a ring-shaped cross section in a plane perpendicular to the first direction, and wherein the directional property is associated with a focal region.

12. The method according to claim 11 wherein the directional property is a location of a center of the focal region.

13. The method according to claim 11 wherein the directional property is a size of the focal region.

14. The method according to claim 11 wherein the directional property is an intensity of the ultrasound energy within the focal region.

15. The method according to claim 1 wherein the ultrasound transducer element has a cross section, in a plane perpendicular to the first direction, that forms a segment of a ring.

16. The method according to claim 1 wherein the ultrasound transducer element is an ultrasound array element of an ultrasound transducer array.

17. The method according to claim 16 wherein the ultrasound transducer array is controlled, via transmit beamforming, to focus the ultrasound energy emitted therefrom to a focal region, and wherein the directional property is a steering angle, and wherein the steering angle is selected such that the ultrasound energy emitted by the ultrasound array element is angled, relative to the first direction, toward the focal region.

18. The method according to claim 17 wherein the steering angle is selected such that the ultrasound energy emitted by the ultrasound array element is directed at the focal region.

19. The method according to claim 17 wherein the focal region is smaller than a diffraction limited focal region that would be achievable according to unidirectional actuation of the ultrasound transducer element.

20. The method according to claim 16 wherein the ultrasound transducer array is formed from a set of concentric ultrasound array elements, each concentric ultrasound array element having a ring-shaped cross section in a plane perpendicular to the first direction.

21. The method according to claim 16 wherein the ultrasound energy is focused at the focal region based on biphasic steering, in the absence of time-of-flight beamforming.

22. The method according to claim 21 wherein the focal region is smaller than a diffraction limited focal region that would be achievable according to time-of-flight beamforming in an absence of biphasic steering.

23. The method according to claim 16 wherein the ultrasound energy is focused at the focal region based on a combination of biphasic steering and time-of-flight beamforming.

24. An ultrasound system comprising:
    an ultrasound transducer element comprising a piezoelectric material, said ultrasound transducer element further comprising a pair of propagation electrodes respectively contacting first opposing surfaces that are perpendicular to a first direction and a pair of lateral electrodes respectively contacting second opposing surfaces that are perpendicular to said first opposing surfaces; and control circuitry operatively coupled to said ultrasound transducer element, said control circuitry comprising at least one processor and associated memory, said memory storing instructions executable by said at least one processor for performing operations comprising:

actuating said ultrasound transducer element according to a first driving waveform and a second driving waveform, the first driving waveform and the second driving waveform having a common frequency, such that the first driving waveform is applied to said propagation electrodes and the second driving waveform is applied to said lateral electrodes; and controlling a directional property of ultrasound energy emitted by said ultrasound transducer element according to at least one of (i) a phase difference between the first driving waveform and the second driving waveform and (ii) an amplitude ratio between the first driving waveform and the second driving waveform.

25. The ultrasound system according to claim 24 wherein said lateral electrodes comprise a first lateral electrode and a second lateral electrode, wherein said first lateral electrode and said second lateral electrode have different respective areas.

26. The ultrasound system according to claim 24 wherein said lateral electrodes comprise a first lateral electrode and a second lateral electrode, wherein said first lateral electrode is spatially offset in the first direction relative to said second lateral electrode.

27. The ultrasound system according to claim 24 wherein said second opposing surfaces are a first lateral surface and a second lateral surface, and wherein at least one of said first lateral surface and said second lateral surface has at least one additional lateral electrode provided thereon; and wherein said control circuitry is configured such that at least one lateral electrode on said first lateral surface and at least one lateral electrode on said second lateral surface are employed to apply the second driving waveform as a potential difference between said first lateral surface and said second lateral surface; and wherein said control circuitry is further configured such that the directional property is controlled, at least in part, by dynamically selecting the lateral electrodes that are employed to apply the potential difference.

28. An ultrasound system comprising:

an ultrasound transducer array, said ultrasound transducer array comprising ultrasound array elements, each ultrasound array element comprising a piezoelectric material, each ultrasound array element further comprising a pair of propagation electrodes respectively contacting first opposing surfaces that are perpendicular to a first direction and a pair of lateral electrodes respectively contacting second opposing surfaces that are perpendicular to said first opposing surfaces; and control circuitry operatively coupled to said ultrasound transducer array, said control circuitry comprising at least one processor and associated memory, said memory storing instructions executable by said at least one processor for performing operations comprising:

while performing transmit beamforming with said ultrasound transducer array:

actuating at least one ultrasound array element with a first respective driving waveform and a second respective driving waveform, the first respective driving waveform and the second respective driving waveform having a common frequency, such that the first respective driving waveform is applied to said propagation electrodes and the second respective driving waveform is applied to said lateral electrodes; and wherein at least one of (i) a respective phase difference between the first respective driving waveform and the second respective driving waveform and (ii) a respective amplitude ratio between the first respective driving waveform and the second respective driving waveform is employed to control a respective directional property of ultrasound energy emitted by said at least one ultrasound array element.

29. A method of directionally controlling an ultrasound transducer element, the ultrasound transducer element comprising a piezoelectric material and further comprising a pair of propagation respectively electrodes respectively contacting first opposing surfaces that are perpendicular to a first direction and a pair of lateral electrodes respectively contacting second opposing surfaces that are perpendicular to the first opposing surfaces, wherein the second opposing surfaces are a first lateral surface and a second lateral surface, and wherein at least one of the first lateral surface and the second lateral surface has at least one additional lateral electrode provided thereon, the method comprising:

actuating the ultrasound transducer element according to a first driving waveform and a second driving waveform, the first driving waveform and the second driving waveform having a common frequency, such that the first driving waveform is applied to the propagation electrodes, and such that at least one lateral electrode on the first lateral surface and at least one lateral electrode on the second lateral surface are employed to apply the second driving waveform as a potential difference between the first lateral surface and the second lateral surface; and controlling a directional property of ultrasound energy emitted by the ultrasound transducer element, at least in part, by dynamically selecting the lateral electrodes that are employed to apply the potential difference.

30. An ultrasound system comprising:

an ultrasound transducer element comprising a piezoelectric material, said ultrasound transducer element further comprising a pair of propagation electrodes respectively contacting first opposing surfaces that are perpendicular to a first direction and a pair of lateral electrodes respectively contacting second opposing surfaces that are perpendicular to said first opposing surfaces, wherein said second opposing surfaces are a first lateral surface and a second lateral surface, and wherein at least one of said first lateral surface and said second lateral surface has at least one additional lateral electrode provided thereon; and control circuitry operatively coupled to said ultrasound transducer element, said control circuitry comprising at least one processor and associated" memory, said memory storing instructions executable by said at least one processor for performing operations comprising:

actuating said ultrasound transducer element according to a first driving waveform and a second driving waveform, the first driving waveform and the second driving waveform having a common frequency, such that the first driving waveform is applied to said propagation electrodes, and such that at least one lateral electrode on said first lateral surface and at least one lateral electrode on said second lateral surface are employed to apply the second driving waveform as a potential difference between said first lateral surface and said second lateral surface; and controlling a directional property of ultrasound energy emitted by said ultrasound transducer element, at least in part, by dynamically selecting the lateral electrodes that are employed to apply the potential difference.

\* \* \* \* \*